(12) United States Patent
Tremblay et al.

(10) Patent No.: US 7,887,793 B2
(45) Date of Patent: Feb. 15, 2011

(54) TREATMENT OF DUCHENNE MUSCULAR DYSTROPHY WITH MYOBLASTS EXPRESSING DYSTROPHIN AND TREATED TO BLOCK MYOSTATIN SIGNALING

(75) Inventors: Jacques P. Tremblay, Stoneham (CA); Basma Fatouma Benabdallah, Saine-Foy (CA)

(73) Assignee: Universite Laval, Quebec (CA)

( * ) Notice: Subject to any disclaimer, the term of this patent is extended or adjusted under 35 U.S.C. 154(b) by 355 days.

(21) Appl. No.: 11/387,435

(22) Filed: Mar. 23, 2006

(65) Prior Publication Data

US 2006/0251632 A1 Nov. 9, 2006

Related U.S. Application Data

(60) Provisional application No. 60/677,324, filed on May 4, 2005.

(30) Foreign Application Priority Data

Mar. 17, 2006 (CA) .................................. 2538208

(51) Int. Cl.
*A01N 63/00* (2006.01)
*A01N 65/00* (2006.01)
*A61K 48/00* (2006.01)

(52) U.S. Cl. .................. 424/93.21; 424/93.1; 514/44 R

(58) Field of Classification Search ........................ None
See application file for complete search history.

(56) References Cited

U.S. PATENT DOCUMENTS

| | | | |
|---|---|---|---|
| 6,284,882 B1 | 9/2001 | Wu-Wong et al. | 536/24.1 |
| 6,368,597 B1 | 4/2002 | Strassmann et al. | 424/158.1 |
| 6,399,312 B2 | 6/2002 | Wu-Wong et al. | 435/6 |
| 6,617,440 B1 | 9/2003 | Findly | 536/23.1 |
| 2001/0049435 A1 | 12/2001 | Wu-Wong et al. | 536/24.1 |
| 2002/0031517 A1 | 3/2002 | Strassmann et al. | 424/158.1 |
| 2003/0138422 A1 | 7/2003 | Aghajanian et al. | 424/145.1 |
| 2004/0030114 A1 | 2/2004 | Findly | 536/23.5 |
| 2005/0014733 A1 | 1/2005 | Whittemore et al. | 514/171 |
| 2006/0030522 A1 | 2/2006 | Knopf et al. | 514/12 |

FOREIGN PATENT DOCUMENTS

| | | |
|---|---|---|
| EP | 01593689 | 10/1985 |
| EP | 01185649 | 4/1987 |
| EP | 1072680 | 7/2000 |
| WO | WO 99/56768 | 11/1999 |
| WO | WO 00/77206 | 12/2000 |
| WO | WO 03/027248 | 4/2003 |
| WO | WO 2004/108157 | 12/2004 |
| WO | WO 2005/051993 | 6/2005 |
| WO | WO 2005/084699 | 9/2005 |

OTHER PUBLICATIONS

Eck et al. (1996) Goodman & Gilman's The Pharmacological Basis of Therapeutics, McGraw-Hill, New York, NY., pp. 77-101.*
Kastrup (2003) Current Gene Therapy, 3: 197-206.*
Game et al (Wien Klin Wochenschr 2001;113:832-38.*
Udinger (1976) Peptide Hormones, University Park Press, Baltimore, MD., pp. 1-7.*
Tanaka, et al. (Apr. 15, 2001) Hum. Mol.. Genet., 10(9):919-26.*
Brett, et al. (1998) European Journal of Pediatric Neurology, 2(2): 77-82, Abstract Only.*
Willer, et al. (2004) Proceedings of National Academy of Sciences, USA., 101(39): 14126-31, Abstract Only.*
Razani, et al. (2000) Journal of Cell Science, 113(pt 2): 2103-09, Abstract Only.*
Dell'Agnola, et al. (2004) Blood, 104(13): 4311-18 (Abstract Only).*
Haslett, et al. (2003) Neurogenetics, 4(4): 163-71 (Abstract Only).*
Cenni, et al. (2005) Journal of Molecular Genetics, 42(3): 214-20 (Abstract Only).*
Nakada, et al. (2004) Pathobiology, 71(1): 43-51.*
Kostova, et al. (2007) Journal of Child Neurology, 22(8): 926-45.*
Leriche-Guerin (2002) Neuromuscular Disorders 12: 167-73.*
Benabdallah, et al. (Jun. 27, 2005) Transplantation, 79(12): 1696-702.*
"Mechanisms of IGF-I and Shh mediated myogenesis," Federal research in progress under Purdue University. (abstract only).
"Molecular mechanisms regulating skeletal muscle growth and differentiation," Federal research in progress under Ohio State University. (abstract only).
Altschul et al., "Basic Local Alignment Search Tool," *J. Mol. Biol.*, 215:403-10, 1990.
Amthor et al., "Follistatin complexes myostatin and antagonises myostatin-mediated inhibition of myogenesis," *Dev. Biol.*, 270(1):19-30, 2004.
Amthor, "The regulation and action of myostatin as a negative regulator of muscle development during avian embryogenesis," *Dev Biol*, 251(2):241-57, 2002.
Bagby, "Programmed limitation of muscle mass by maternal protein restriction: mechanisms and impact on offspring fat deposition," Federal research in progress under the Department of Veterans Affairs. (abstract only).
Bass et al., "Growth factors controlling muscle development," *Domest Anim Endocrinol*, 17(2-3):191-7, 1999.
Benabdallah et al., "Blocking the myostatin signal permits to improve the success of myoblast transplantation in mdx," *AFM (Asssociations Francaise Contre Les Myopathies)*, Communication No. 170, May 9 to 19, 2005.
Benabdallah et al., "Overexpression of the myostatin antagonist follistatin in normal myoblasts genetically modified with a lentivirus," *AFM (Asssociations Francaise Contre Les Myopathies)* May 9 to 19, 2005.

(Continued)

*Primary Examiner*—Robert M Kelly
(74) *Attorney, Agent, or Firm*—Fulbright & Jaworski L.L.P.

(57) ABSTRACT

The invention relates to methods and materials for enhancing muscle mass or for the treatment of muscle disease in a subject, comprising introducing a cell which has a lower than normal level of myostatin signalling, into the subject.

17 Claims, 26 Drawing Sheets

OTHER PUBLICATIONS

Bishop et al., "The therapeutic potential of agents that inactivate myostatin," *Expert Opinion on Investigational Drugs*, 14(9):1099-1106, 2005. (abstract only).

Blau et al., "Defective myoblasts identified in Duchenne muscular dystrophy," *Proc. Natl. Acad Sci.* USA, 80:4856-4860, 1983.

Bogdanovich et al, "Functional improvement of dystrophic muscle by myostatin blockade," *Nature*, 420(6914):418-21, 2002.

Bogdanovich et al., "Myostatin propetide-mediated amelioration of dystrophic pathophysiology," *FASEB J*, 19(6):543-9, 2005.

Brown et al., "RNA Interference in Mammalian Cell Culture: Design, Execution and Analysis of the siRNA Effect," *TechNotes*, 9(1):3-5, Obtained from www.biocompare.com on Jun. 20, 2006.

Brown, "Hybridization analysis of DNA blots," *Current Protocols in Molecular Biology*, 2.10.1-2.10.16, Supplement 21, 1993, Copyright 2000 by John, Wiley & Sons, Inc.

Brummelkamp et al., "A system for stable expression of short interfering RNAs in mammalian cells," *Science*, 296(5567):550-553, 2002.

Brussee et al., "Muscle fibers of mdx mice are more vulnerable to exercise that those of normal mice," *Neuromuscul. Disord.*, 7:487-492, 1997.

Camirand et al., "Novel Duchenne muscular dystrophy treatment through myoblast transplantation tolerance with anti-CD45RB, anti-CD154 and Mixed chimerism," *Am. J. Transplant*, 4:1255, 2004.

Caplen et al., "Specific inhibition of gene expression by small double-stranded RNAs in invertebrate and vertbrate systems," *Proc. Natl. Acad. Sci.* USA, 98:9742-9747, 2001.

Cook, "Transcriptional effects of chronic Akt activation in the heart," *J Biol Chem*, 277(25):22528-33, 2002.

Emery, "Duchenne muscular dystrophy-Meryon's disease," *Neuromuscul, Disord.*, 3:263-266, 1993.

Fernyhough et al., "Nutrients found in some bodybuilding supplements do not influence postnatal muscle stem cell activity," *FASEB Journal*, 18(4-5):Abst. 616.14, 2004.

Forbes et al., "Myostatin auto-regulates its expression by feedback loop through Smad7 dependent mechanism," *Journal of Cellular Physiology*, 206(1):264-272, 2005. (abstract only).

Gonzalez-Cadavid and Bhasin, "Role of myostatin in metabolism," *Curr. Opin. Clin. Nutr. Metab. Care*, 7(4):451-457, 2004.

Hallauer et al., "Complex fiber-type-specific expression of fast skeletal muscle troponin I gene constructs in transgenic mice," *Development*, 119:691-701, 1993.

Hamer et al., "Evans Blue Dye as an in vivo marker of myofibre damage: optimising parameters for detecting initial myofibre membrane permeability," *J. Anat.*, 200:69-79, 2002.

Hammond et al., "Argonaute2, a link between genetic and biochemical analyses of RNAi," *Science*, 293:1146-1150, 2001.

Hamrick, "Effects of myostatin deficiency on bone strength," Federal research in progress under the Medical College of Georgia and the National Institute of Arthritis and Musculoskeletal and Skin Diseases, 2004. (abstract only).

Hamrick, "Increased bone mineral density in the femora of GDF8 knockout mice," *Anat Rec*, 272A(1);388-91, 2003.

Henikoff and Henikoff, "Amino acid substitution matrices from protein blocks," *Proc. Natl. Acad. Sci.* USA, 89:10915-10919, 1992.

Hoffman et al., "Dystrophin: The protein product of the Duchenne muscular dystrophy locus," *Cell*, 51:919-928, 1987.

Huard et al., "Gene transfer into skeletal muscles by isogenic myoblasts," *Hum. Gene Ther.*, 5:949-58, 1994.

Huard et al., "Transplantation of dermal fibroblasts expressing myoD1 in mouse muscles," *Biochem. Biophys. Res. Commun.*, 248:648-654, 1998.

Huet et al., "Skeletal muscle cell hypertrophy induced by inhibitors of metalloproteases; myostatin as a potential mediator," *Am J Physiol Cell Physiol*, 281(5):C1624-34, 2001.

Jiang et al., "Characterization and identification of the inhibitory domain of GDF-8 propetide," *Biochem. Biophys. Res. Commun.*, 315:525-531, 2004.

Joulia et al., "Mechanisms involved in the inhibition of myoblast proliferation and differentiation by myostatin," *Exp Cell Res*, 286(2):263-75, 2003.

Kim et al., "Impact of resistance loading on myostatin expression and cell cycle regulation in young and older men and women," *American Journal of Physiology*, 288(6):E1110-E1119, 2005.

Kinoshita et al., "Very efficient myoblast allotransplantation in mice under fk506 immunosuppression," *Muscle Nerve*, 17:1407-1415, 1994.

Kocamis, "The effects of myostatin gene inhibition by an antisense oligodeoxynucleotide and tis immunocytochemical localization in C2C12 myoblasts," *Kafkas Universitesi Veteriner Fakultesi Dergisi*, 10(1):87-90, 2004. (abstract only).

Langley et al., "Myostatin inhibits myoblast differentiation by down-regulating MyoD expression," *J Biol Chem*, 277(51):49831-40, 2002.

Langley et al., "Myostatin inhibits rhabdomyosarcoma cell proliferation through an Rb-independent pathway," *Oncogene*, 23(2):524-34, 2004.

Lee and McPherron, "Regulation of myostatin activity and muscle growth," *Proc. Natl. Acad. Sci.* USA, 98(16):9306-9311, 2001.

Lee et al., "Expression of small interfering RNAs targeted against HIV-1 rev transcripts in human cells," *Nat Biotechnol.*, 20(5):500-505, 2002.

Lee et al., "Regulation of muscle growth by multiple ligands signaling through activin type II receptors," *Proceedings of the National Academy of Sciences of the United States of America*, 102(50):18117-22, 2005.

Lee, "Regulation of muscle mass by myostatin," *Ann Rev Cell Dev Biol*, 20:61-86, 2004.

Lee, "Role of myostatin in cachexia," Federal research in progress under Johns Hopkins University and the National Cancer Institute, 2004. (abstract only).

Lin et al., "P27 knockout mice: reduced myostatin muscle and altered adipogenesis," *Biochem Biophys Res Commun*, 300(4):938-42, 2003.

Matzuk et al., "Multiple defects and perinatal death in mice deficient in follistatin," *Nature*, 374:360-363, 1995.

McPherron et al, "Novel members of the transforming growth factor-beta superfamily (GDF-11, myostatin, differentiation," Dissertation Abstract, John Hopkins University, 59-01B:88, 1998.

Mendias et al., "Myostatin increases procollagen content in tendon-derived fibroblast cells," *FASEB Journal*, 19(5, Suppl. S, Part 2):A1118, 2005. (abstract only).

Mimata and Sumino, "A promising future therapeutic strategy for urinary stress incontinence," *Nishinihon Journal of Urology*, 67(4):184-194, 2005. (abstract only).

Miyagashi and Taira, "Development and application of siRNA expression vector," *Nucleic Acids Res. Suppl.*, (2):113-114, 2002.

Needleman and Wunsch, "A general method applicable to the search for similarities in the amino acid sequence of two proteins," *J. Mol. Biol.*, 48:443-453, 1970.

Nielsen et al., "Sequence-selective recognition of DNA by strand displacement with a thymine-substituted polyamide," *Science*, 254:1497-1500, 1991.

Ohlendieck and Campbell, "Dystrophin-associated proteins are greatly reduced in skeletal muscle from mdx mice,"*J. Cell Biol.*, 115:1685-1694, 1991.

Paddison et al., "Stable suppression of gene expression by RNAi in mammalian cells," *Proc. Natl. Acad. Sci.* USA, 99(3):1443-1448, 2002.

Patel and Amthor, "The function of myostatin and strategies of myostatin blockade-new hope for therapies aimed at promoting growth of skeletal muscle," *Neuromuscul Disord*, 15(2):117-26, 2005.

Paul et al., "Effective expression of small interfering RNA in human cells," *Nat. Biotechnol.*, 20(5):505-508, 2002.

Pearson and Lipman, "Improved tools for biological sequence comparison," *Proc. Natl. Acad. Sci.* USA, 85:2444-2448, 1988.

Qu-Petersen et al., "Identification of a novel population of muscle stem cells in mice: potential for muscle regeneration," *J. Cell Biol.*, 157:851-864, 2002.

Ricaud et al., "Inhibition of autocrine secretion of myostatin enhances terminal differentiation in human rhabdomyosarcoma cells," *Oncogene*, 22(51):8221-8232, 2003.

Rios et al., "Myostatin is an inhibitor of myogenic differentiation," *Am J Physiol Cell Physiol*, 282(5):C993-9, 2002.

Rosenzweig, "Role of myostatin in cardiac hypertrophy and failure," Federal research in progress under Massachusetts General Hospital and the National Heart Lung, and Blood Institute, 2004. (abstract only).

Sharma et al., "A review of recent findings on myostatin, a gene which controls muscle growth," *Proceedings of the New Zealand Society of Animal Production*, 59(0):291-293, 1999. (abstract only).

Sharp, "RNA interference-2001," *Genes Dev.*, 15:485-490, 2001.

Skuk and Tremblay, "Myoblast transplantation: the current status of a potential therapeutic tool for myopathies," *J. Muscle Res. Cell Motil.*, 24:285-300, 2003.

Skuk and Tremblay, "Progress in myoblast transplantation: a potential treatment of dystrophies," *Microsc. Res. Tech.*, 48:213-222, 2000.

Smith and Waterman, "Comparison of biosequences," *Adv. Appl. Math.*, 2:482-489, 1981.

Sui et al., "A DNA vector-based RNAi technology to suppress gene expression in mammalian cells," *Proc. Natl. Acad. Sci. USA*, 99(8):5515-5520, 2002.

Taylor et al., "Myostatin regulates expression of genes involved in skeletal muscel cell proliferation and differentiation," *Journal of Investigative Medicine*, 49(1):69A(#372), 2001.

Tesfaye et al., "Review article- Factors affecting morphology of skeletal muscles," *Acta Veterinaria Brno*, 74(1):153-159, 2005. (abstract only).

Thies et al., "GDF-8 propeptide binds to DF-8 and antagonizes biological activity by inhibiting GDF-8 receptor binding," *Growth Factors*, 18(4):251-9, 2001.

Thomas et al., "Myostatin, a negative regulator of muscle growth, functions by inhibiting myoblast proliferation," *Proceedings of the New Zealand Society of Animal Production*, 60:85-89, 2000. (abstract only).

Tobin and Celeste, "Myostatin, a negative regulator of muscle mass: implications for muscle degenerative diseases," *Curr Opin Pharmacol*, 5(3):328-32, 2005. (abstract only).

Torrente et al., "Intraarterial injection of muscle-derived $CD34^+Sca-1^+$ stem cells restores dystrophin in *mdx* mice," *J. Cell Biol.*, 152:335-348, 2001.

Wagner et al., "Muscle regeneration in the prolonged absence of myostatin," *Proc Natl Acad Sci USA*, 102(7):2519-24, 2005.

Wagner, "Muscle regeneration through myostatin inhibition," *Curr Opin Rheumatol*, 17(6):720-4, 2005. (abstract only).

Walsh and Celeste, "Myostatin: a modulator of skeletal-muscle stem cells," *Biochemical Society Transactions*, 33(0:1513-1517, 2005.

Whittemore et al., "Inhibition of myostatin in adult mice increases skeletal muscle mass and strength," *Biochem Biophys Res Commun*, 300(4):965-71, 2003.

Yu et al., "RNA interference by expression of short-interfering RNAs and hairpin RNAs in mammalian cells," *Proc. Natl. Acad. Sci. USA*, 99(9):6047-6052, 2002.

Zhang et al, "Altered expressino of myostatin gene in the progressive muscular dystrophy patients," *Acta Genetica Sinica*, 32(8):779-783, 2005. (abstract only).

Zhu et al., "Dominant negative myostatin produced hypertrophy without hyperplasia in muscle," *FEBS Lett*, 474(1):71-5, 2000.

Thu et al., "Myostatin signaling through Smad2, Smad3 and Smad4 is regulated by the inhibitory Smad7 by a negative feedback mechanism," *Cytokine*, 26(6):262-272, 2004.

\* cited by examiner

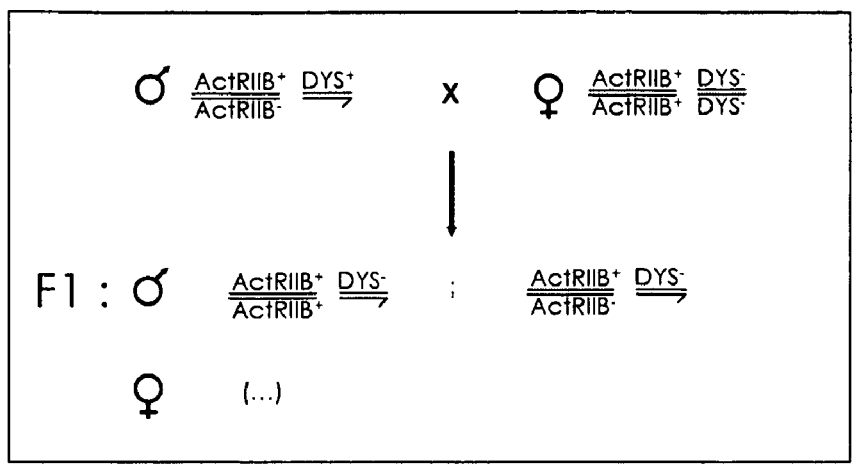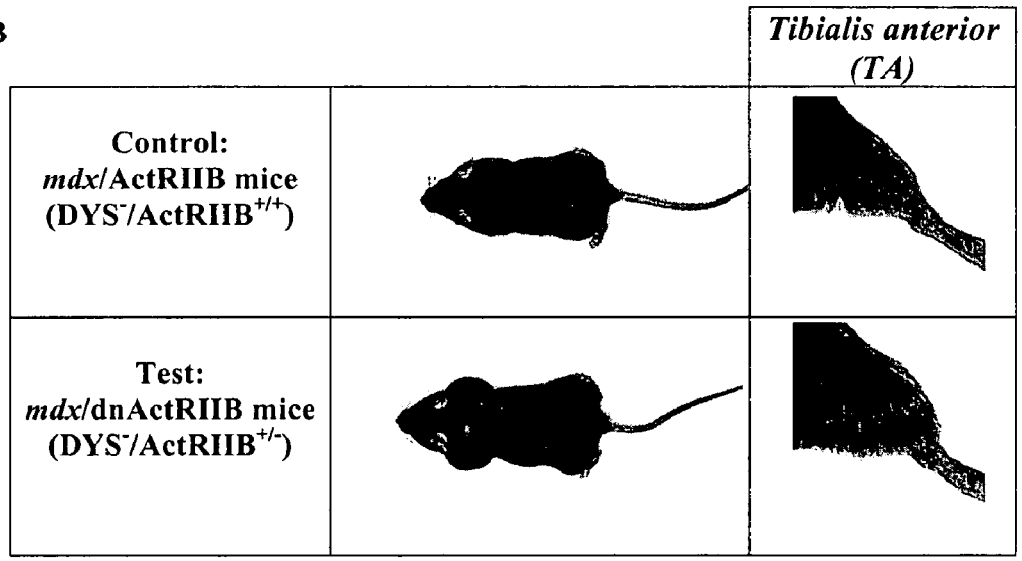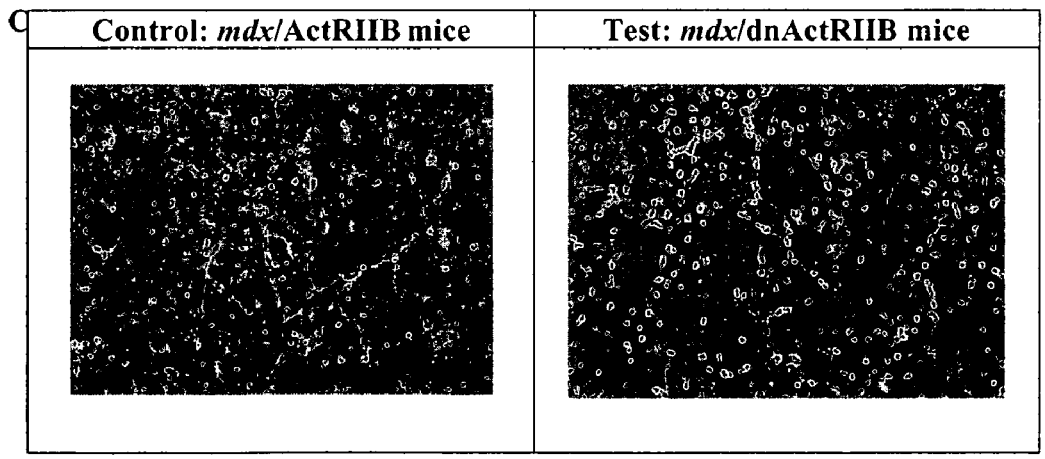
Fig.1

A
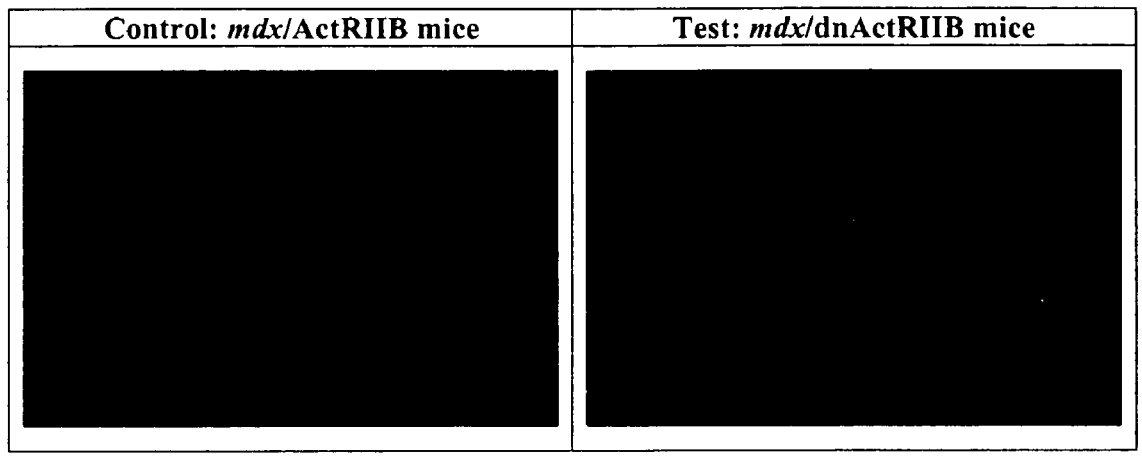
B
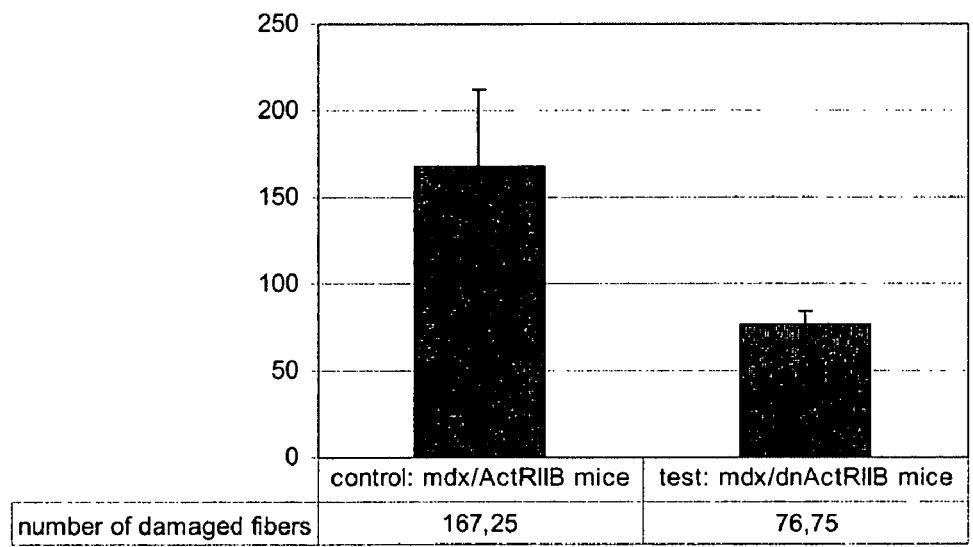
*Fig.2*

A
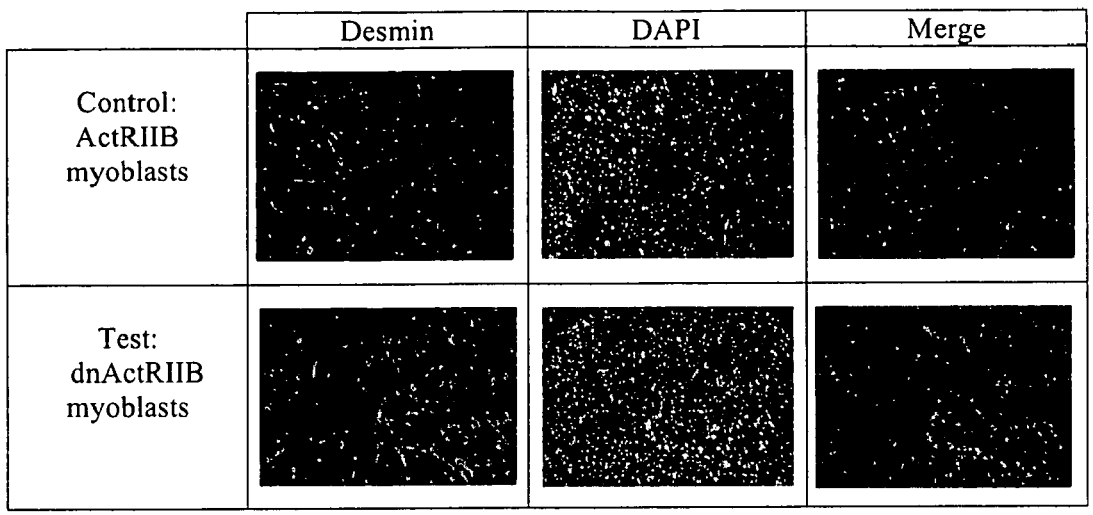
B
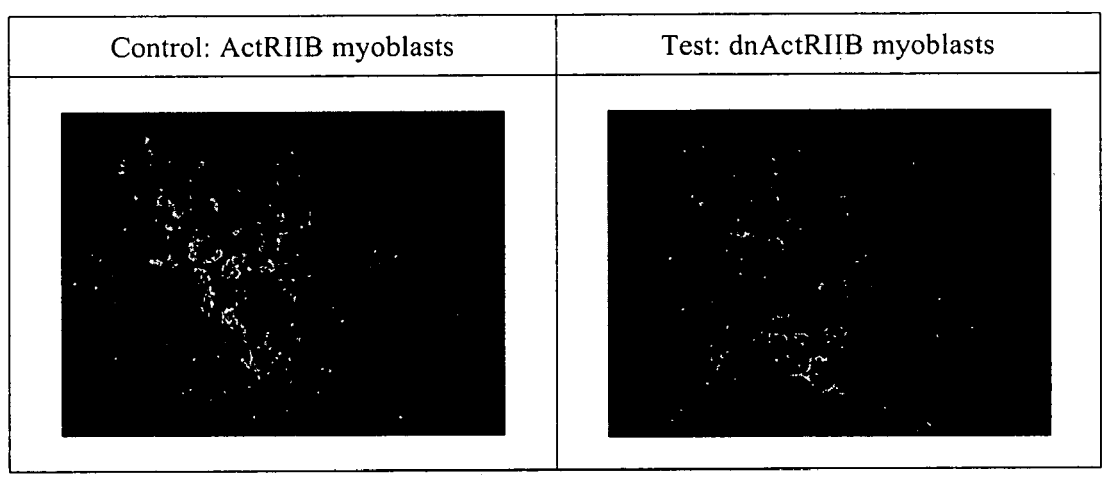
C
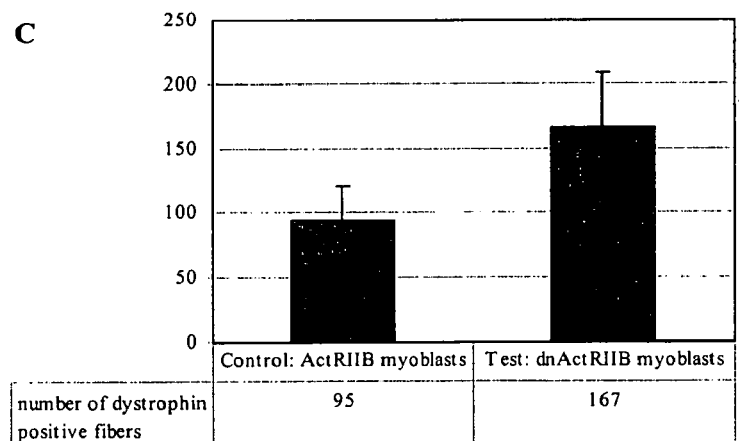
*Fig. 4*

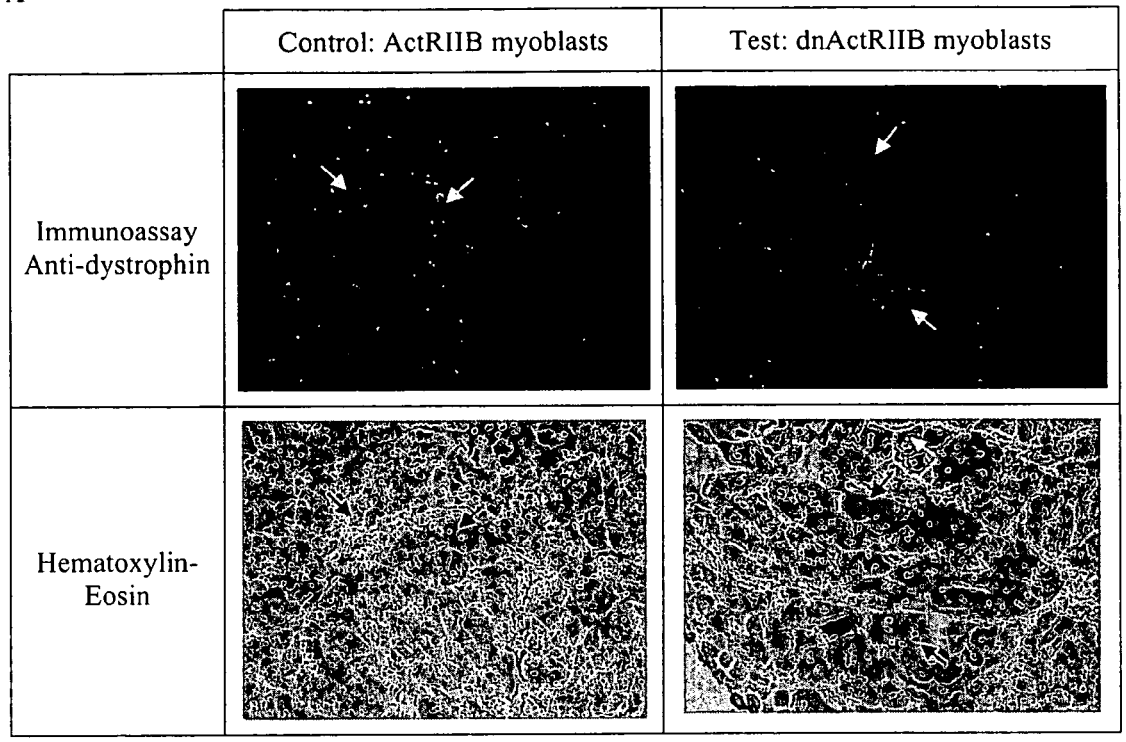
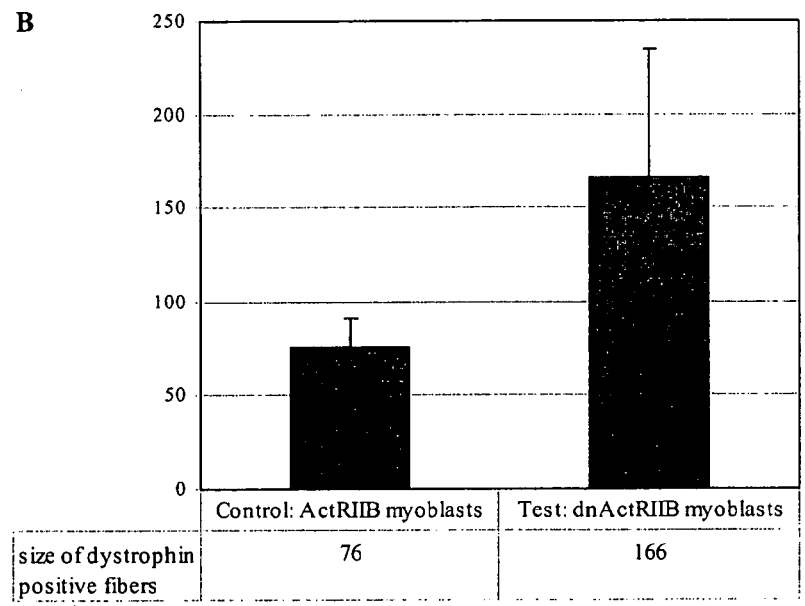
*Fig. 5*

A
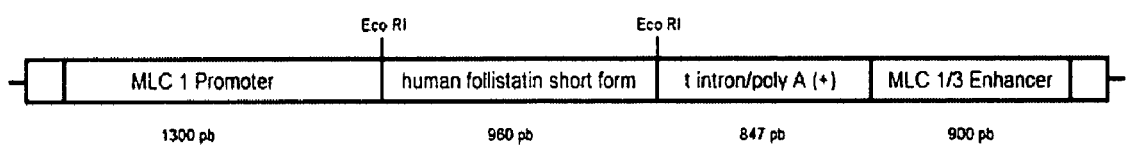
B 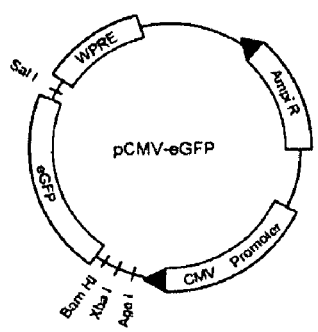 C 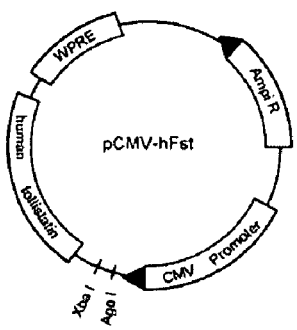
*Fig. 11*

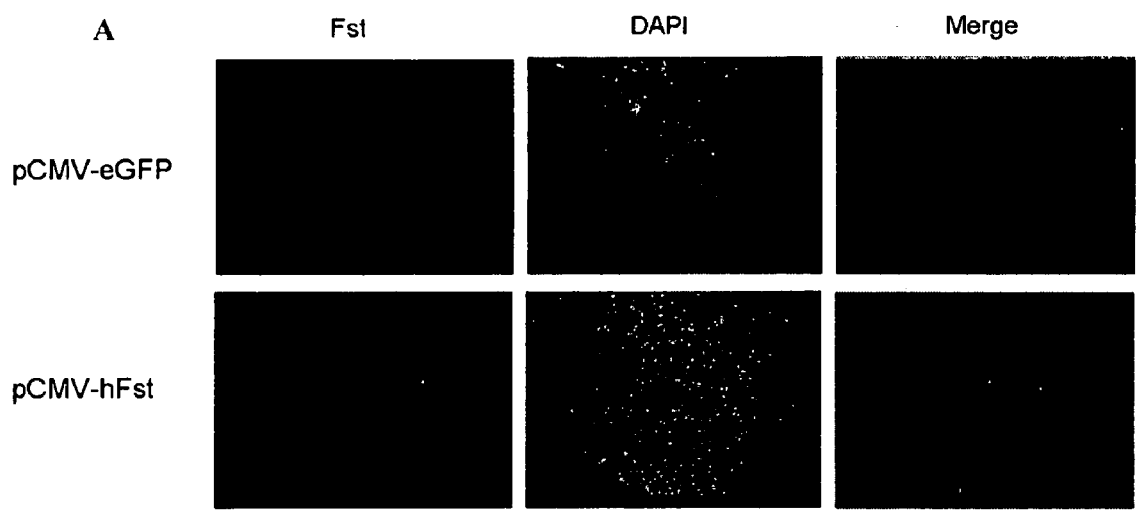
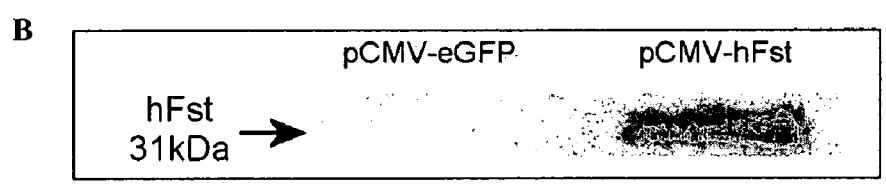
*Fig. 12*

A
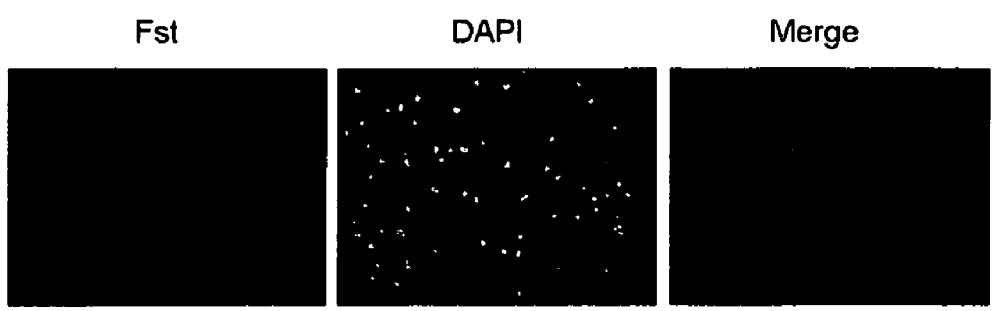
B
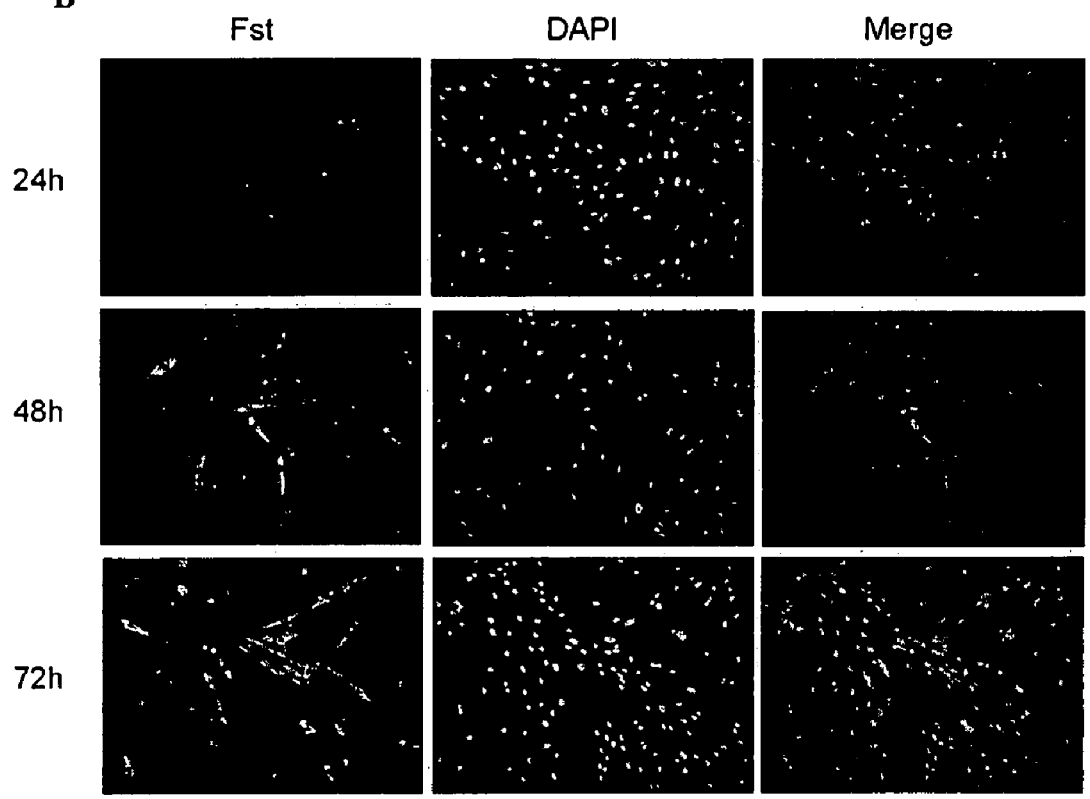
Fig. 13

DNA and polypeptide sequences of human myostatin (Genbank accession No. NM_00529).

DNA sequence encoding human myostatin (SEQ ID NO:1).
Coding sequence defined by positions 134 to 1261:

```
   1 agattcactg gtgtggcaag ttgtctctca gactgtacat gcattaaaat tttgcttggc
  61 attactcaaa agcaaaagaa aagtaaaagg aagaaacaag aacaagaaaa aagattatat
 121 tgattttaaa atcatgcaaa aactgcaact ctgtgtttat atttacctgt ttatgctgat
 181 tgttgctggt ccagtggatc taaatgagaa cagtgagcaa aagaaaatg tggaaaaaga
 241 ggggctgtgt aatgcatgta cttggagaca aaacactaaa tcttcaagaa tagaagccat
 301 taagatacaa atcctcagta aacttcgtct ggaaacagct cctaacatca gcaaagatgt
 361 tataagacaa ctttacccca agctcctcc actccgggaa ctgattgatc agtatgatgt
 421 ccagagggat gacagcagcg atggctcttt ggaagatgac gattatcacg ctacaacgga
 481 aacaatcatt accatgccta cagagtctga ttttctaatg caagtggatg gaaaacccaa
 541 atgttgcttc tttaaattta gctctaaaat acaatacaat aaagtagtaa aggcccaact
 601 atggatatat tgagacccg tcgagactcc tacaacagtg tttgtgcaaa tcctgagact
 661 catcaaacct atgaaagacg gtacaaggta tactggaatc cgatctctga aacttgacat
 721 gaacccaggc actggtattt ggcagagcat tgatgtgaag acagtgttgc aaaattggct
 781 caaacaacct gaatccaact taggcattga aataaaagct ttagatgaga atggtcatga
 841 tcttgctgta accttcccag gaccaggaga agatgggctg aatccgtttt tagaggtcaa
 901 ggtaacagac acaccaaaaa gatccagaag ggattttggt cttgactgtg atgagcactc
 961 aacagaatca cgatgctgtc gttaccctct aactgtggat tttgaagctt tggatgggga
1021 ttggattatc gctcctaaaa gatataaggc caattactgc tctggagagt gtgaatttgt
1081 atttttacaa aaatatcctc atactcatct ggtacaccaa gcaaacccca gaggttcagc
1141 aggcccttgc tgtactccca aaagatgtc tccaattaat atgctatatt taatggcaa
1201 agaacaaata atatatggga aaattccagc gatggtagta gaccgctgtg gtgctcatg
1261 agatttatat taagcgttca taacttccta aaacatggaa ggttttcccc tcaacaattt
1321 tgaagctgtg aaattaagta ccacaggcta taggcctaga gtatgctaca gtcacttaag
1381 cataagctac agtatgtaaa ctaaaagggg gaatatatgc aatggttggc atttaaccat
1441 ccaaacaaat catacaagaa agttttatga ttccagagt ttttgagcta gaaggagatc
1501 aaattacatt tatgttccta tatattacaa catcggcgag gaaatgaaag cgattctcct
1561 tgagttctga tgaattaaag gagtatgctt taaagtctat ttcttaaag ttttgtttaa
1621 tatttacaga aaaatccaca tacagtattg gtaaaatgca ggattgttat ataccatcat
1681 tcgaatcatc cttaaacact tgaatttata ttgtatggta gtatacttgg taagataaaa
1741 ttccacaaaa atagggatgg tgcagcatat gcaatttcca ttcctattat aattgacaca
1801 gtacattaac aatccatgcc aacggtgcta atacgatagg ctgaatgtct gaggctacca
1861 ggtttatcac ataaaaaaca ttcagtaaaa tagtaagttt ctcttttctt cagggcatt
1921 ttcctacacc tccaaatgag gaatggattt tctttaatgt aagaagaatc attttctag
1981 aggttggctt tcaattctgt agcatacttg gagaaactgc attatcttaa.aaggcagtca
2041 aatggtgttt gttttatca aaatgtcaaa ataacatact tggagaagta tgtaattttg
2101 tctttggaaa attacaacac tgcctttgca acactgcagt ttttatggta aaataataga
2161 aatgatcgac tctatcaata ttgtataaaa agactgaaac aatgcattta tataatatgt
2221 atacaatatt gttttgtaaa taagtgtctc cttttttatt tactttggta tatttttaca
2281 ctaaggacat ttcaaattaa gtactaaggc acaagacat gtcatgcatc acagaaaagc
2341 aactacttat atttcagagc aaattagcag attaaatagt ggtcttaaaa ctccatatgt
2401 taatgattag atggttatat tacaatcatt ttatatttt tacatgatt aacattcact
2461 tatggattca tgatggctgt ataagtgaa tttgaaattt caatggttta ctgtcattgt
2521 gtttaaatct caacgttcca ttatttaat acttgcaaaa acattactaa gtataccaaa
2581 ataattgact ctattatctg aaatgaagaa taaactgatg ctatctcaac aataactgtt
2641 acttttattt tataatttga taatgaatat atttctgcat ttatttactt ctgtttgta
2701 aattgggatt tgttaatca aatttattgt actatgacta aatgaaatta tttcttacat
2761 ctaatttgta gaaacagtat aagttatatt aaagtgtttt cacattttt tgaaagacaa
2821 aaa
```

*Fig. 14*

Polypeptide sequence of human myostatin (SEQ ID NO:2).
Translation of coding sequence defined by positions 134 to
1261 in DNA sequence above:

MQKLQLCVYIYLFMLIVAGPVDLNENSEQKENVEKEGLCNACTWRQNTKSSRIEAIKIQILSKLRLETAP
NISKDVIRQLLPKAPPLRELIDQYDVQRDDSSDGSLEDDDYHATTETIITMPTESDFLMQVDGKPKCCFF
KFSSKIQYNKVVKAQLWIYLRPVETPTTVFVQILRLIKPMKDGTRYTGIRSLKLDMNPGTGIWQSIDVKT
VLQNWLKQPESNLGIEIKALDENGHDLAVTFPGPGEDGLNPFLEVKVTDTPKRSRRDFGLDCDEHSTESR
CCRYPLTVDFEAFGWDWIIAPKRYKANYCSGECEFVFLQKYPHTHLVHQANPRGSAGPCCTPTKMSPINM
LYFNGKEQIIYGKIPAMVVDRCGCS

*Fig. 14*: continued

DNA and polypeptide sequences of human ActRIIB (Genbank accession No. NM_001106).

DNA sequence encoding human myostatin (SEQ ID NO:3). Coding sequence defined by positions 5 to 1543. Signal peptide defined by positions 5 to 58. Mature peptide defined by positions 59 to 1540. Extracellular domain defined by positions 59 to 406. Transmembrane domain defined by positions 407 to 484. Cytoplasmic domain defined by positions 485 to 1540. Protein kinase domain defined by positions 572 to 1444:

```
   1 gaacatgacg gcgccctggg tggccctcgc cctcctctgg ggatcgctgt ggcccggctc
  61 tgggcgtggg gaggctgaga cacgggagtg catctactac aacgccaact gggagctgga
 121 gcgcaccaac cagagcggcc tggagcgctg cgaaggcgag caggacaagc ggctgcactg
 181 ctacgcctcc tgggccaaca gctctggcac catcgagctc gtgaagaagg gctgctggct
 241 agatgacttc aactgctacg ataggcagga gtgtgtggcc actgaggaga acccccaggt
 301 gtacttctgc tgctgtgaag gcaacttctg caacgagcgc ttcactcatt tgccagaggc
 361 tgggggcccg gaagtcacgt acgagccacc cccgacagcc ccaccctgc tcacggtgct
 421 ggcctactca ctgctgccca tcgggggcct ttccctcatc gtcctgctgg ccttttggat
 481 gtaccggcat cgcaagcccc cctacggtca tgtggacatc catgaggacc tgggcctcc
 541 accaccatcc cctctggtgg gcctgaagcc actgcagctg ctggagatca aggctcgggg
 601 gcgctttggc tgtgtctgga aggcccagct catgaatgac tttgtagctg tcaagatctt
 661 cccactccag gacaagcagt cgtggcagag tgaacgggag atcttcagca cacctggcat
 721 gaagcacgag aacctgctac agttcattgc tgccgagaag cgaggctcca acctcgaagt
 781 agagctgtgg ctcatcacgg ccttccatga caagggctcc ctcacggatt acctcaaggg
 841 gaacatcatc acatggaacg aactgtgtca tgtagcagag acgatgtcac gaggcctctc
 901 atacctgcat gaggatgtgc cctggtgccg tggcgagggc cacaagccgt ctattgccca
 961 cagggacttt aaaagtaaga atgtattgct gaagagcgac ctcacagccg tgctggctga
1021 ctttggcttg gctgttcgat tgagccagg gaaacctcca ggggacaccc acggacaggt
1081 aggcacgaga cggtacatgg ctcctgaggt gctcgaggga gccatcaact tccagagaga
1141 tgccttcctg cgcattgaca tgtatgccat ggggttggtg ctgtgggagc ttgtgtctcg
1201 ctgcaaggct gcagacggac ccgtggatga gtacatgctg cccctttgagg aagagattgg
1261 ccagcaccct tcgttggagg agctgcagga ggtggtggtg cacaagaaga tgaggcccac
1321 cattaaagat cactggttga aacacccggg cctggcccag ctttgtgtga ccatcgagga
1381 gtgctggac catgatgcag aggctcgctt gtccgcgggc tgtgtggagg agcgggtgtc
1441 cctgattcgg aggtcggtca acggcactac ctcggactgt ctcgtttcc tggtgacctc
1501 tgtcaccaat gtggacctgc cccctaaaga gtcaagcatc taagcccagg acatgagtgt
1561 ctctccagac tcagtggatc tgaa
```

Polypeptide sequence of human ActRIIB (SEQ ID NO:4). Translation of coding sequence defined by positions 5 to 1543 in DNA sequence above:

MTAPWVALALLWGSLWPGSGRGEAETRECIYYNANWELERTNQSGLERCEGEQDKRLHCYASWANSSGTI
ELVKKGCWLDDFNCYDRQECVATEENPQVYFCCCEGNFCNERFTHLPEAGGPEVTYEPPPTAPTLLTVLA
YSLLPIGGLSLIVLLAFWMYRHRKPPYGHVDIHEDPGPPPPSPLVGLKPLQLLEIKARGRFGCVWKAQLM
NDFVAVKIFPLQDKQSWQSEREIFSTPGMKHENLLQFIAAEKRGSNLEVELWLITAFHDKGSLTDYLKGN
IITWNELCHVAETMSRGLSYLHEDVPWCRGEGHKPSIAHRDFKSKNVLLKSDLTAVLADFGLAVRFEPGK
PPGDTHGQVGTRRYMAPEVLEGAINFQRDAFLRIDMYAMGLVLWELVSRCKAADGPVDEYMLPFEEEIGQ
HPSLEELQEVVVHKKMRPTIKDHWLKHPGLAQLCVTIEECWDHDAEARLSAGCVEERVSLIRRSVNGTTS
DCLVSLVTSVTNVDLPPKESSI

*Fig. 15*

A
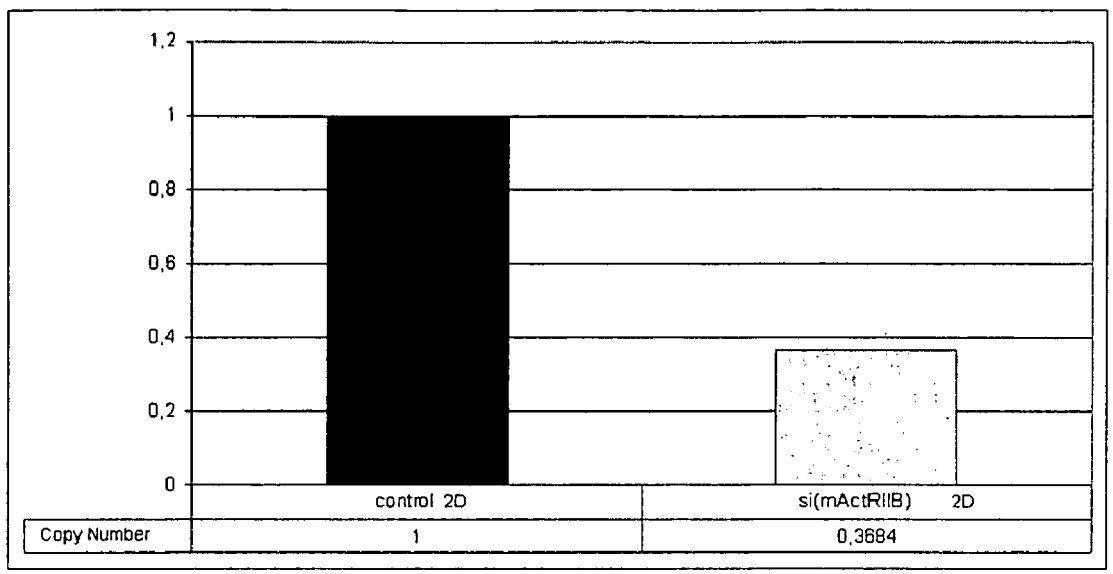
B
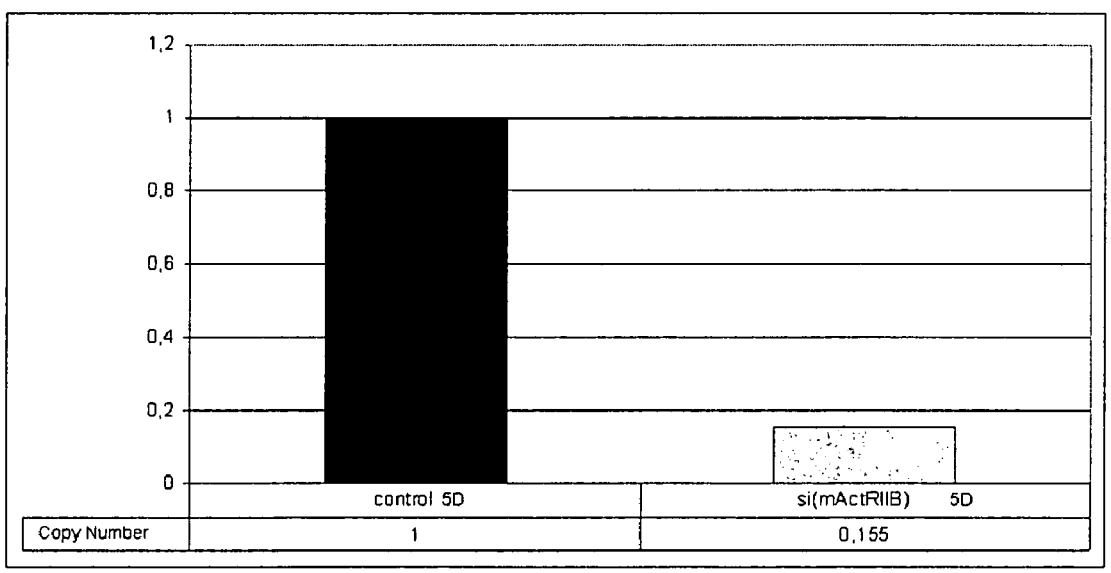
Figure 16

A
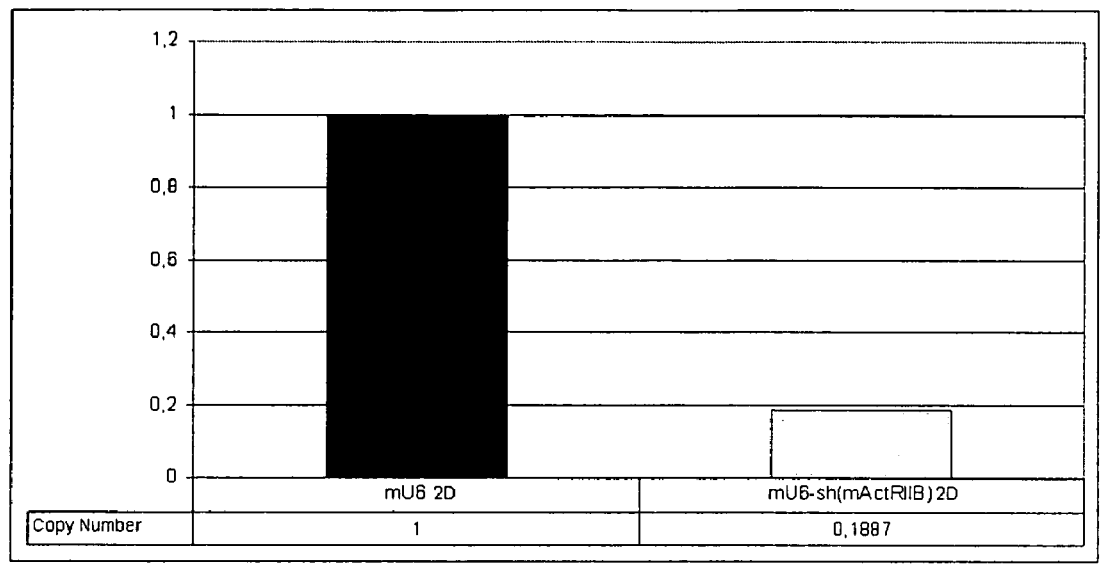
B
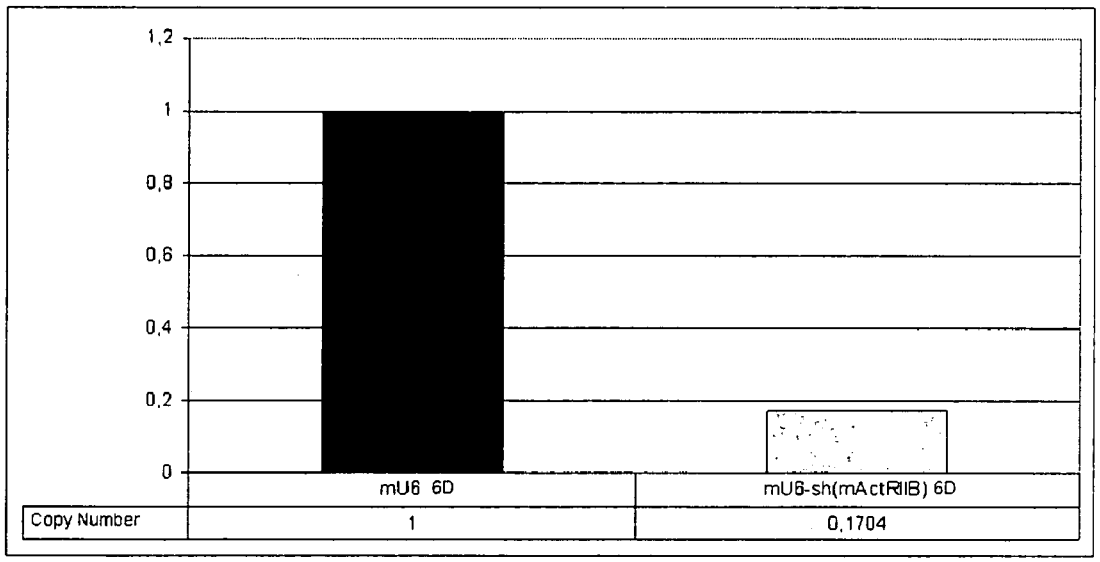
Figure 18

A
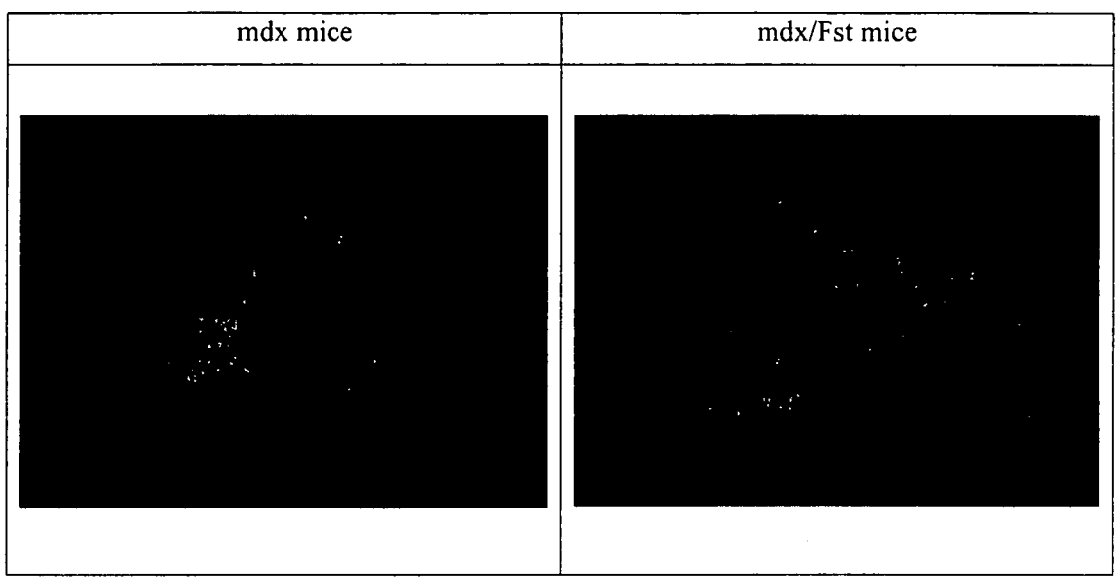
B
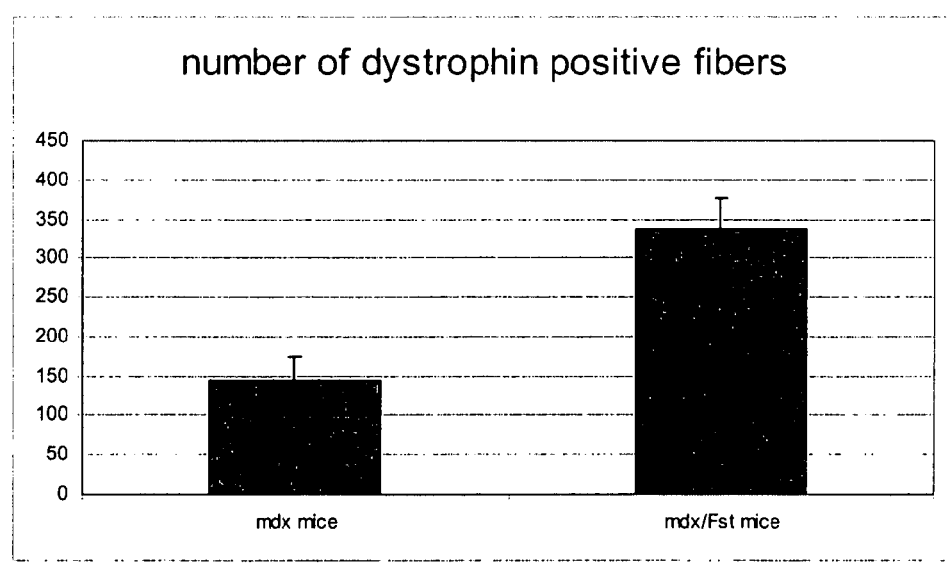
Figure 21

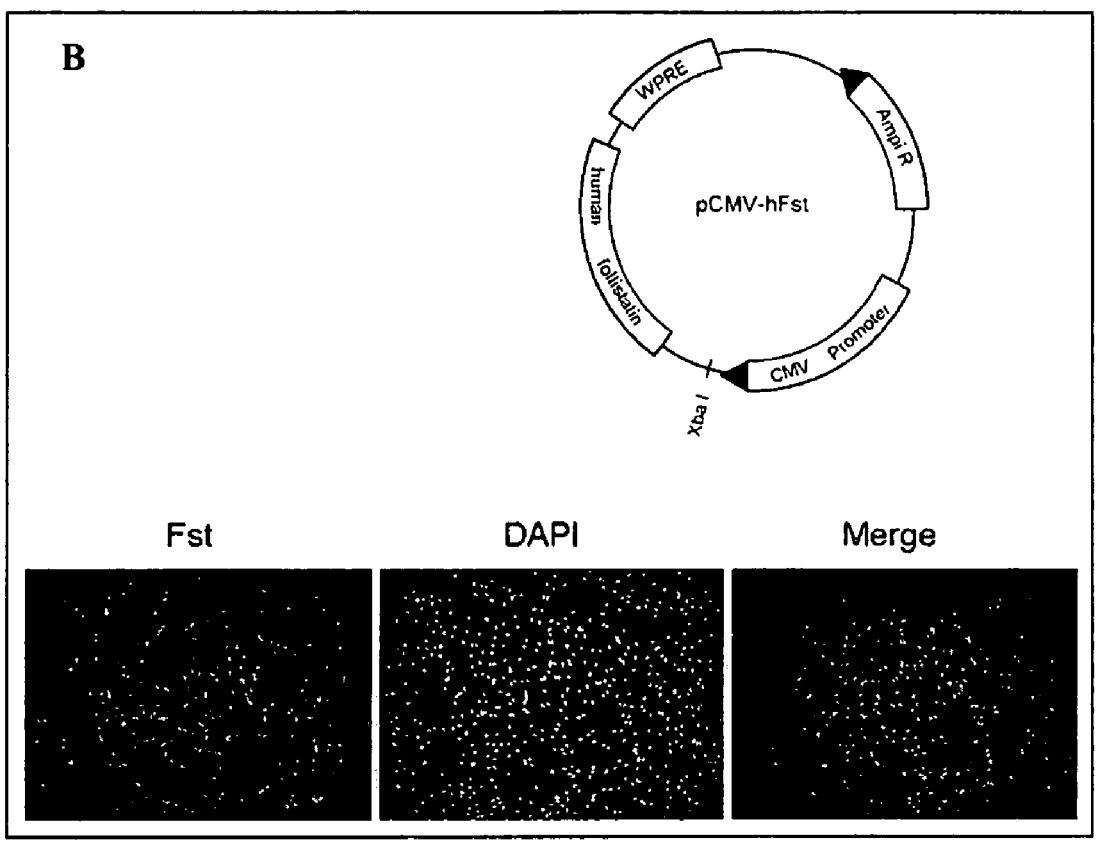
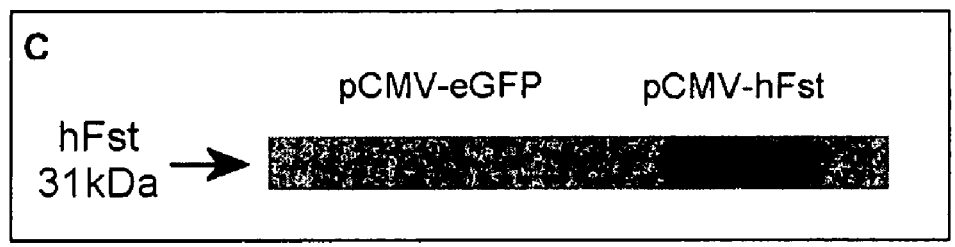
Figure 22B and C

Homo sapiens follistatin (FST), transcript variant FST317. ACCESSION NO.NM_006350

A: Follistatin DNA (SEQ ID NO:5)

```
   1 gctcctcgcc ccgcgcctgc ccccaggatg gtccgcgcga ggcaccagcc gggtgggctt
  61 tgcctcctgc tgctgctgct ctgccagttc atggaggacc gcagtgccca ggctgggaac
 121 tgctggctcc gtcaagcgaa gaacggccgc tgccaggtcc tgtacaagac cgaactgagc
 181 aaggaggagt gctgcagcac cggccggctg agcacctcgt ggaccgagga ggacgtgaat
 241 gacaacacac tcttcaagtg gatgattttc aacggggggcg cccccaactg catccctgt
 301 aaagaaacgt gtgagaacgt ggactgtgga cctgggaaaa aatgccgaat gaacaagaag
 361 aacaaacccc gctgcgtctg cgccccggat tgttccaaca tcacctggaa gggtccagtc
 421 tgcgggctgg atgggaaaac ctaccgcaat gaatgtgcac tcctaaaggc aagatgtaaa
 481 gagcagccag aactggaagt ccagtaccaa ggcagatgta aaaagacttg tcgggatgtt
 541 ttctgtccag gcagctccac atgtgtggtg gaccagacca ataatgccta ctgtgtgacc
 601 tgtaatcgga tttgcccaga gcctgcttcc tctgagcaat atctctgtgg aatgatgga
 661 gtcacctact ccagtgcctg ccacctgaga aaggctacct gctgctggg cagatctatt
 721 ggattagcct atgagggaaa gtgtatcaaa gcaaagtcct gtgaagatat ccagtgcact
 781 ggtgggaaaa aatgtttatg ggatttcaag gttgggagag gccggtgttc cctctgtgat
 841 gagctgtgcc ctgacagtaa gtcggatgag cctgtctgtg ccagtgacaa tgccacttat
 901 gccagcgagt gtgccatgaa ggaagctgcc tgctcctcag gtgtgctact ggaagtaaag
 961 cactccggat cttgcaactg aatctgcccg taaaacctga gccattgatt cttcagaact
1021 ttctgcagtt tttgacttca tagattatgc tttaaaaaat ttttttaac ttattgcata
1081 acagcagatg ccaaaaacaa aaaaagcatc tcactgcaag tcacataaaa atgcaacgct
1141 gtaatatggc tgtatcagag ggctttgaaa acatacactg agctgcttct gcgctgttgt
1201 tgtccgtatt taaacaacag ctcccctgta ttcccccatc tagccatttc ggaagacacc
1261 gaggaagagg aggaagatga agaccaggac tacagctttc ctatatcttc tattctagag
1321 tggtaaactc tctataagtg ttcagtgttc acatagcctt tgtgcaaaaa aaaaaaaaaa
1381 aaaaaa
```

B: Follistatin protein sequence (SEQ ID NO:6)

MVRARHQPGGLCLLLLLLCQFMEDRSAQAGNCWLRQAKNGRCQVLYKTELSKEECCSTGRL
STSWTEEDVNDNTLFKWMIFNGGAPNCIPCKETCENVDCGPGKKCRMNKKNKPRCVCAPDC
SNITWKGPVCGLDGKTYRNECALLKARCKEQPELEVQYQGRCKKTCRDVFCPGSSTCVVDQ
TNNAYCVTCNRICPEPASSEQYLCGNDGVTYSSACHLRKATCLLGRSIGLAYEGKCIKAKSCE
DIQCTGGKKCLWDFKVGRGRCSLCDELCPDSKSDEPVCASDNATYASECAMKEAACSSGVLL
EVKHSGSCN

Figure 24

SEQUENCE LISTING

```
<160> NUMBER OF SEQ ID NOS: 13

<210> SEQ ID NO 1
<211> LENGTH: 2823
<212> TYPE: DNA
<213> ORGANISM: Homo sapiens
<220> FEATURE:
<221> NAME/KEY: CDS
<222> LOCATION: (134)..(1261)

<400> SEQUENCE: 1
agattcactg gtgtggcaag ttgtctctca gactgtacat gcattaaaat tttgcttggc      60
attactcaaa agcaaaagaa aagtaaaagg aagaaacaag aacaagaaaa aagattatat     120
tgattttaaa atc atg caa aaa ctg caa ctc tgt gtt tat att tac ctg        169
             Met Gln Lys Leu Gln Leu Cys Val Tyr Ile Tyr Leu
               1               5                  10 ttt atg ctg att gtt gct ggt cca gtg gat cta aat gag aac agt gag       217
Phe Met Leu Ile Val Ala Gly Pro Val Asp Leu Asn Glu Asn Ser Glu
              15                  20                  25 caa aaa gaa aat gtg gaa aaa gag ggg ctg tgt aat gca tgt act tgg       265
Gln Lys Glu Asn Val Glu Lys Glu Gly Leu Cys Asn Ala Cys Thr Trp
         30                  35                  40 aga caa aac act aaa tct tca aga ata gaa gcc att aag ata caa atc       313
Arg Gln Asn Thr Lys Ser Ser Arg Ile Glu Ala Ile Lys Ile Gln Ile
 45                  50                  55                  60 ctc agt aaa ctt cgt ctg gaa aca gct cct aac atc agc aaa gat gtt       361
Leu Ser Lys Leu Arg Leu Glu Thr Ala Pro Asn Ile Ser Lys Asp Val
                 65                  70                  75 ata aga caa ctt tta ccc aaa gct cct cca ctc cgg gaa ctg att gat       409
Ile Arg Gln Leu Leu Pro Lys Ala Pro Pro Leu Arg Glu Leu Ile Asp
             80                  85                  90 cag tat gat gtc cag agg gat gac agc agc gat ggc tct ttg gaa gat       457
Gln Tyr Asp Val Gln Arg Asp Asp Ser Ser Asp Gly Ser Leu Glu Asp
         95                 100                 105
```

```
                                                              -continued
gac gat tat cac gct aca acg gaa aca atc att acc atg cct aca gag       505
Asp Asp Tyr His Ala Thr Thr Glu Thr Ile Ile Thr Met Pro Thr Glu
    110             115                 120 tct gat ttt cta atg caa gtg gat gga aaa ccc aaa tgt tgc ttc ttt       553
Ser Asp Phe Leu Met Gln Val Asp Gly Lys Pro Lys Cys Cys Phe Phe
125             130                 135                 140 aaa ttt agc tct aaa ata caa tac aat aaa gta gta aag gcc caa cta       601
Lys Phe Ser Ser Lys Ile Gln Tyr Asn Lys Val Val Lys Ala Gln Leu
                145                 150                 155 tgg ata tat ttg aga ccc gtc gag act cct aca aca gtg ttt gtg caa       649
Trp Ile Tyr Leu Arg Pro Val Glu Thr Pro Thr Thr Val Phe Val Gln
            160                 165                 170 atc ctg aga ctc atc aaa cct atg aaa gac ggt aca agg tat act gga       697
Ile Leu Arg Leu Ile Lys Pro Met Lys Asp Gly Thr Arg Tyr Thr Gly
        175                 180                 185 atc cga tct ctg aaa ctt gac atg aac cca ggc act ggt att tgg cag       745
Ile Arg Ser Leu Lys Leu Asp Met Asn Pro Gly Thr Gly Ile Trp Gln
    190                 195                 200 agc att gat gtg aag aca gtg ttg caa aat tgg ctc aaa caa cct gaa       793
Ser Ile Asp Val Lys Thr Val Leu Gln Asn Trp Leu Lys Gln Pro Glu
205             210                 215                 220 tcc aac tta ggc att gaa ata aaa gct tta gat gag aat ggt cat gat       841
Ser Asn Leu Gly Ile Glu Ile Lys Ala Leu Asp Glu Asn Gly His Asp
                225                 230                 235 ctt gct gta acc ttc cca gga cca gga gaa gat ggg ctg aat ccg ttt       889
Leu Ala Val Thr Phe Pro Gly Pro Gly Glu Asp Gly Leu Asn Pro Phe
            240                 245                 250 tta gag gtc aag gta aca gac aca cca aaa aga tcc aga agg gat ttt       937
Leu Glu Val Lys Val Thr Asp Thr Pro Lys Arg Ser Arg Arg Asp Phe
        255                 260                 265 ggt ctt gac tgt gat gag cac tca aca gaa tca cga tgc tgt cgt tac       985
Gly Leu Asp Cys Asp Glu His Ser Thr Glu Ser Arg Cys Cys Arg Tyr
    270                 275                 280 cct cta act gtg gat ttt gaa gct ttt gga tgg gat tgg att atc gct      1033
Pro Leu Thr Val Asp Phe Glu Ala Phe Gly Trp Asp Trp Ile Ile Ala
285             290                 295                 300 cct aaa aga tat aag gcc aat tac tgc tct gga gag tgt gaa ttt gta      1081
Pro Lys Arg Tyr Lys Ala Asn Tyr Cys Ser Gly Glu Cys Glu Phe Val
                305                 310                 315 ttt tta caa aaa tat cct cat act cat ctg gta cac caa gca aac ccc      1129
Phe Leu Gln Lys Tyr Pro His Thr His Leu Val His Gln Ala Asn Pro
            320                 325                 330 aga ggt tca gca ggc cct tgc tgt act ccc aca aag atg tct cca att      1177
Arg Gly Ser Ala Gly Pro Cys Cys Thr Pro Thr Lys Met Ser Pro Ile
        335                 340                 345 aat atg cta tat ttt aat ggc aaa gaa caa ata ata tat ggg aaa att      1225
Asn Met Leu Tyr Phe Asn Gly Lys Glu Gln Ile Ile Tyr Gly Lys Ile
    350                 355                 360 cca gcg atg gta gta gac cgc tgt ggg tgc tca tga gatttatatt           1271
Pro Ala Met Val Val Asp Arg Cys Gly Cys Ser
365             370                 375 aagcgttcat aacttcctaa aacatggaag gttttcccct caacaatttt gaagctgtga    1331
aattaagtac cacaggctat aggcctagag tatgctacag tcacttaagc ataagctaca    1391
gtatgtaaac taaagggggg aatatatgca atggttggca tttaaccatc caaacaaatc    1451
atacaagaaa gttttatgat ttccagagtt tttgagctag aaggagatca aattacattt    1511
atgttcctat atattacaac atcggcgagg aaatgaaagc gattctcctt gagttctgat    1571
gaattaaagg agtatgcttt aaagtctatt tctttaaagt tttgtttaat atttacagaa    1631
```

-continued

```
aaatccacat acagtattgg taaaatgcag gattgttata taccatcatt cgaatcatcc    1691
ttaaacactt gaatttatat tgtatggtag tatacttggt aagataaaat tccacaaaaa    1751
tagggatggt gcagcatatg caatttccat tcctattata attgacacag tacattaaca    1811
atccatgcca acggtgctaa tacgataggc tgaatgtctg aggctaccag gtttatcaca    1871
taaaaaacat tcagtaaaat agtaagtttc tcttttcttc aggggcattt tcctacacct    1931
ccaaatgagg aatggatttt ctttaatgta agaagaatca ttttctaga ggttggcttt     1991 caattctgta gcatacttgg agaaactgca ttatcttaaa aggcagtcaa atggtgtttg    2051
tttttatcaa aatgtcaaaa taacatactt ggagaagtat gtaattttgt ctttggaaaa    2111
ttacaacact gcctttgcaa cactgcagtt tttatggtaa aataatagaa atgatcgact    2171
ctatcaatat tgtataaaaa gactgaaaca atgcatttat ataatatgta tacaatattg    2231
ttttgtaaat aagtgtctcc ttttttattt actttggtat attttttacac taaggacatt    2291 tcaaattaag tactaaggca caaagacatg tcatgcatca cagaaaagca actacttata    2351
tttcagagca aattagcaga ttaaatagtg gtcttaaaac tccatatgtt aatgattaga    2411
tggttatatt acaatcattt tatatttttt tacatgatta acattcactt atggattcat    2471
gatggctgta taaagtgaat ttgaaatttc aatggtttac tgtcattgtg tttaaatctc    2531
aacgttccat tatttaata cttgcaaaaa cattactaag tataccaaaa taattgactc      2591
tattatctga aatgaagaat aaactgatgc tatctcaaca ataactgtta cttttatttt    2651
ataatttgat aatgaatata tttctgcatt tatttacttc tgttttgtaa attgggattt    2711
tgttaatcaa atttattgta ctatgactaa atgaaattat ttcttacatc taatttgtag    2771
aaacagtata agttatatta aagtgttttc acatttttt gaaagacaaa aa             2823
```

<210> SEQ ID NO 2
<211> LENGTH: 375
<212> TYPE: PRT
<213> ORGANISM: Homo sapiens

<400> SEQUENCE: 2

```
Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160
```

```
Arg Pro Val Glu Thr Pro Thr Thr Val Phe Val Gln Ile Leu Arg Leu
            165                 170                 175

Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
            195                 200             205

Lys Thr Val Leu Gln Asn Trp Leu Lys Gln Pro Glu Ser Asn Leu Gly
            210                 215             220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
                275                 280                 285

Asp Phe Glu Ala Phe Gly Trp Asp Trp Ile Ile Ala Pro Lys Arg Tyr
290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
                340                 345                 350

Phe Asn Gly Lys Glu Gln Ile Ile Tyr Gly Lys Ile Pro Ala Met Val
                355                 360                 365

Val Asp Arg Cys Gly Cys Ser
                370                 375

<210> SEQ ID NO 3
<211> LENGTH: 1584
<212> TYPE: DNA
<213> ORGANISM: Homo sapiens
<220> FEATURE:
<221> NAME/KEY: CDS
<222> LOCATION: (5)..(1543)

<400> SEQUENCE: 3 gaac atg acg gcg ccc tgg gtg gcc ctc gcc ctc ctc tgg gga tcg ctg      49
     Met Thr Ala Pro Trp Val Ala Leu Ala Leu Leu Trp Gly Ser Leu
     1               5                   10                  15 tgg ccc ggc tct ggg cgt ggg gag gct gag aca cgg gag tgc atc tac      97
Trp Pro Gly Ser Gly Arg Gly Glu Ala Glu Thr Arg Glu Cys Ile Tyr
                20                  25                  30 tac aac gcc aac tgg gag ctg gag cgc acc aac cag agc ggc ctg gag     145
Tyr Asn Ala Asn Trp Glu Leu Glu Arg Thr Asn Gln Ser Gly Leu Glu
            35                  40                  45 cgc tgc gaa ggc gag cag gac aag cgg ctg cac tgc tac gcc tcc tgg     193
Arg Cys Glu Gly Glu Gln Asp Lys Arg Leu His Cys Tyr Ala Ser Trp
        50                  55                  60 gcc aac agc tct ggc acc atc gag ctc gtg aag aag ggc tgc tgg cta     241
Ala Asn Ser Ser Gly Thr Ile Glu Leu Val Lys Lys Gly Cys Trp Leu
65                  70                  75 gat gac ttc aac tgc tac gat agg cag gag tgt gtg gcc act gag gag     289
Asp Asp Phe Asn Cys Tyr Asp Arg Gln Glu Cys Val Ala Thr Glu Glu
80                  85                  90                  95 aac ccc cag gtg tac ttc tgc tgc tgt gaa ggc aac ttc tgc aac gag     337
Asn Pro Gln Val Tyr Phe Cys Cys Cys Glu Gly Asn Phe Cys Asn Glu
```

-continued

|  |  |  |  |  |  |  | 100 |  |  |  | 105 |  |  |  | 110 |  |  |  |
|---|---|---|---|---|---|---|---|---|---|---|---|---|---|---|---|---|---|---|
| cgc | ttc | act | cat | ttg | cca | gag | gct | ggg | ggc | ccg | gaa | gtc | acg | tac | gag | | | 385 |
| Arg | Phe | Thr | His | Leu | Pro | Glu | Ala | Gly | Gly | Pro | Glu | Val | Thr | Tyr | Glu | | | |
|  |  |  | 115 |  |  |  | 120 |  |  |  | 125 |  |  |  |  | | | |

| cca | ccc | ccg | aca | gcc | ccc | acc | ctg | ctc | acg | gtg | ctg | gcc | tac | tca | ctg | | | 433 |
|---|---|---|---|---|---|---|---|---|---|---|---|---|---|---|---|---|---|---|
| Pro | Pro | Pro | Thr | Ala | Pro | Thr | Leu | Leu | Thr | Val | Leu | Ala | Tyr | Ser | Leu | | | |
|  |  | 130 |  |  |  | 135 |  |  |  | 140 |  |  |  |  |  | | | |

| ctg | ccc | atc | ggg | ggc | ctt | tcc | ctc | atc | gtc | ctg | ctg | gcc | ttt | tgg | atg | | | 481 |
|---|---|---|---|---|---|---|---|---|---|---|---|---|---|---|---|---|---|---|
| Leu | Pro | Ile | Gly | Gly | Leu | Ser | Leu | Ile | Val | Leu | Leu | Ala | Phe | Trp | Met | | | |
|  | 145 |  |  |  | 150 |  |  |  | 155 |  |  |  |  |  |  | | | |

| tac | cgg | cat | cgc | aag | ccc | ccc | tac | ggt | cat | gtg | gac | atc | cat | gag | gac | | | 529 |
|---|---|---|---|---|---|---|---|---|---|---|---|---|---|---|---|---|---|---|
| Tyr | Arg | His | Arg | Lys | Pro | Pro | Tyr | Gly | His | Val | Asp | Ile | His | Glu | Asp | | | |
| 160 |  |  |  | 165 |  |  |  | 170 |  |  |  | 175 |  |  |  | | | |

| cct | ggg | cct | cca | cca | cca | tcc | cct | ctg | gtg | ggc | ctg | aag | cca | ctg | cag | | | 577 |
|---|---|---|---|---|---|---|---|---|---|---|---|---|---|---|---|---|---|---|
| Pro | Gly | Pro | Pro | Pro | Pro | Ser | Pro | Leu | Val | Gly | Leu | Lys | Pro | Leu | Gln | | | |
|  |  |  | 180 |  |  |  | 185 |  |  |  | 190 |  |  |  |  | | | |

| ctg | ctg | gag | atc | aag | gct | cgg | ggg | cgc | ttt | ggc | tgt | gtc | tgg | aag | gcc | | | 625 |
|---|---|---|---|---|---|---|---|---|---|---|---|---|---|---|---|---|---|---|
| Leu | Leu | Glu | Ile | Lys | Ala | Arg | Gly | Arg | Phe | Gly | Cys | Val | Trp | Lys | Ala | | | |
|  |  | 195 |  |  |  | 200 |  |  |  | 205 |  |  |  |  |  | | | |

| cag | ctc | atg | aat | gac | ttt | gta | gct | gtc | aag | atc | ttc | cca | ctc | cag | gac | | | 673 |
|---|---|---|---|---|---|---|---|---|---|---|---|---|---|---|---|---|---|---|
| Gln | Leu | Met | Asn | Asp | Phe | Val | Ala | Val | Lys | Ile | Phe | Pro | Leu | Gln | Asp | | | |
|  | 210 |  |  |  | 215 |  |  |  | 220 |  |  |  |  |  |  | | | |

| aag | cag | tcg | tgg | cag | agt | gaa | cgg | gag | atc | ttc | agc | aca | cct | ggc | atg | | | 721 |
|---|---|---|---|---|---|---|---|---|---|---|---|---|---|---|---|---|---|---|
| Lys | Gln | Ser | Trp | Gln | Ser | Glu | Arg | Glu | Ile | Phe | Ser | Thr | Pro | Gly | Met | | | |
| 225 |  |  |  | 230 |  |  |  | 235 |  |  |  |  |  |  |  | | | |

| aag | cac | gag | aac | ctg | cta | cag | ttc | att | gct | gcc | gag | aag | cga | ggc | tcc | | | 769 |
|---|---|---|---|---|---|---|---|---|---|---|---|---|---|---|---|---|---|---|
| Lys | His | Glu | Asn | Leu | Leu | Gln | Phe | Ile | Ala | Ala | Glu | Lys | Arg | Gly | Ser | | | |
| 240 |  |  |  | 245 |  |  |  | 250 |  |  |  | 255 |  |  |  | | | |

| aac | ctc | gaa | gta | gag | ctg | tgg | ctc | atc | acg | gcc | ttc | cat | gac | aag | ggc | | | 817 |
|---|---|---|---|---|---|---|---|---|---|---|---|---|---|---|---|---|---|---|
| Asn | Leu | Glu | Val | Glu | Leu | Trp | Leu | Ile | Thr | Ala | Phe | His | Asp | Lys | Gly | | | |
|  |  |  | 260 |  |  |  | 265 |  |  |  | 270 |  |  |  |  | | | |

| tcc | ctc | acg | gat | tac | ctc | aag | ggg | aac | atc | atc | aca | tgg | aac | gaa | ctg | | | 865 |
|---|---|---|---|---|---|---|---|---|---|---|---|---|---|---|---|---|---|---|
| Ser | Leu | Thr | Asp | Tyr | Leu | Lys | Gly | Asn | Ile | Ile | Thr | Trp | Asn | Glu | Leu | | | |
|  |  | 275 |  |  |  | 280 |  |  |  | 285 |  |  |  |  |  | | | |

| tgt | cat | gta | gca | gag | acg | atg | tca | cga | ggc | ctc | tca | tac | ctg | cat | gag | | | 913 |
|---|---|---|---|---|---|---|---|---|---|---|---|---|---|---|---|---|---|---|
| Cys | His | Val | Ala | Glu | Thr | Met | Ser | Arg | Gly | Leu | Ser | Tyr | Leu | His | Glu | | | |
|  | 290 |  |  |  | 295 |  |  |  | 300 |  |  |  |  |  |  | | | |

| gat | gtg | ccc | tgg | tgc | cgt | ggc | gag | ggc | cac | aag | ccg | tct | att | gcc | cac | | | 961 |
|---|---|---|---|---|---|---|---|---|---|---|---|---|---|---|---|---|---|---|
| Asp | Val | Pro | Trp | Cys | Arg | Gly | Glu | Gly | His | Lys | Pro | Ser | Ile | Ala | His | | | |
| 305 |  |  |  | 310 |  |  |  | 315 |  |  |  |  |  |  |  | | | |

| agg | gac | ttt | aaa | agt | aag | aat | gta | ttg | ctg | aag | agc | gac | ctc | aca | gcc | | | 1009 |
|---|---|---|---|---|---|---|---|---|---|---|---|---|---|---|---|---|---|---|
| Arg | Asp | Phe | Lys | Ser | Lys | Asn | Val | Leu | Leu | Lys | Ser | Asp | Leu | Thr | Ala | | | |
| 320 |  |  |  | 325 |  |  |  | 330 |  |  |  | 335 |  |  |  | | | |

| gtg | ctg | gct | gac | ttt | ggc | ttg | gct | gtt | cga | ttt | gag | cca | ggg | aaa | cct | | | 1057 |
|---|---|---|---|---|---|---|---|---|---|---|---|---|---|---|---|---|---|---|
| Val | Leu | Ala | Asp | Phe | Gly | Leu | Ala | Val | Arg | Phe | Glu | Pro | Gly | Lys | Pro | | | |
|  |  |  | 340 |  |  |  | 345 |  |  |  | 350 |  |  |  |  | | | |

| cca | ggg | gac | acc | cac | gga | cag | gta | ggc | acg | aga | cgg | tac | atg | gct | cct | | | 1105 |
|---|---|---|---|---|---|---|---|---|---|---|---|---|---|---|---|---|---|---|
| Pro | Gly | Asp | Thr | His | Gly | Gln | Val | Gly | Thr | Arg | Arg | Tyr | Met | Ala | Pro | | | |
|  |  | 355 |  |  |  | 360 |  |  |  | 365 |  |  |  |  |  | | | |

| gag | gtg | ctc | gag | gga | gcc | atc | aac | ttc | cag | aga | gat | gcc | ttc | ctg | cgc | | | 1153 |
|---|---|---|---|---|---|---|---|---|---|---|---|---|---|---|---|---|---|---|
| Glu | Val | Leu | Glu | Gly | Ala | Ile | Asn | Phe | Gln | Arg | Asp | Ala | Phe | Leu | Arg | | | |
|  | 370 |  |  |  | 375 |  |  |  | 380 |  |  |  |  |  |  | | | |

| att | gac | atg | tat | gcc | atg | ggg | ttg | gtg | ctg | tgg | gag | ctt | gtg | tct | cgc | | | 1201 |
|---|---|---|---|---|---|---|---|---|---|---|---|---|---|---|---|---|---|---|
| Ile | Asp | Met | Tyr | Ala | Met | Gly | Leu | Val | Leu | Trp | Glu | Leu | Val | Ser | Arg | | | |
| 385 |  |  |  | 390 |  |  |  | 395 |  |  |  |  |  |  |  | | | |

| tgc | aag | gct | gca | gac | gga | ccc | gtg | gat | gag | tac | atg | ctg | ccc | ttt | gag | | | 1249 |
|---|---|---|---|---|---|---|---|---|---|---|---|---|---|---|---|---|---|---|
| Cys | Lys | Ala | Ala | Asp | Gly | Pro | Val | Asp | Glu | Tyr | Met | Leu | Pro | Phe | Glu | | | |
| 400 |  |  |  | 405 |  |  |  | 410 |  |  |  | 415 |  |  |  | | | |

| gaa | gag | att | ggc | cag | cac | cct | tcg | ttg | gag | gag | ctg | cag | gag | gtg | gtg | | | 1297 |
|---|---|---|---|---|---|---|---|---|---|---|---|---|---|---|---|---|---|---|

-continued

```
Glu Glu Ile Gly Gln His Pro Ser Leu Glu Glu Leu Gln Glu Val Val
                420                 425                 430 gtg cac aag aag atg agg ccc acc att aaa gat cac tgg ttg aaa cac      1345
Val His Lys Lys Met Arg Pro Thr Ile Lys Asp His Trp Leu Lys His
        435                 440                 445 ccg ggc ctg gcc cag ctt tgt gtg acc atc gag gag tgc tgg gac cat      1393
Pro Gly Leu Ala Gln Leu Cys Val Thr Ile Glu Glu Cys Trp Asp His
    450                 455                 460 gat gca gag gct cgc ttg tcc gcg ggc tgt gtg gag gag cgg gtg tcc      1441
Asp Ala Glu Ala Arg Leu Ser Ala Gly Cys Val Glu Glu Arg Val Ser
465                 470                 475                 480 ctg att cgg agg tcg gtc aac ggc act acc tcg gac tgt ctc gtt tcc      1489
Leu Ile Arg Arg Ser Val Asn Gly Thr Thr Ser Asp Cys Leu Val Ser
                485                 490                 495 ctg gtg acc tct gtc acc aat gtg gac ctg ccc cct aaa gag tca agc      1537
Leu Val Thr Ser Val Thr Asn Val Asp Leu Pro Pro Lys Glu Ser Ser
            500                 505                 510 atc taa gcccaggaca tgagtgtctc tccagactca gtggatctga a                1584
Ile

<210> SEQ ID NO 4
<211> LENGTH: 512
<212> TYPE: PRT
<213> ORGANISM: Homo sapiens

<400> SEQUENCE: 4

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
            35                  40                  45

Cys Glu Gly Glu Gln Asp Lys Arg Leu His Cys Tyr Ala Ser Trp Ala
        50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240
```

```
His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 5
<211> LENGTH: 1386
<212> TYPE: DNA
<213> ORGANISM: Homo sapiens
<220> FEATURE:
<221> NAME/KEY: CDS
<222> LOCATION: (28)..(981)

<400> SEQUENCE: 5
gctcctcgcc ccgcgcctgc ccccagg atg gtc cgc gcg agg cac cag ccg ggt      54
                        Met Val Arg Ala Arg His Gln Pro Gly
                        1               5 ggg ctt tgc ctc ctg ctg ctg ctc tgc cag ttc atg gag gac cgc           102
Gly Leu Cys Leu Leu Leu Leu Leu Cys Gln Phe Met Glu Asp Arg
10              15                  20                  25 agt gcc cag gct ggg aac tgc tgg ctc cgt caa gcg aag aac ggc cgc       150
Ser Ala Gln Ala Gly Asn Cys Trp Leu Arg Gln Ala Lys Asn Gly Arg
                30                  35                  40 tgc cag gtc ctg tac aag acc gaa ctg agc aag gag gag tgc tgc agc       198
Cys Gln Val Leu Tyr Lys Thr Glu Leu Ser Lys Glu Glu Cys Cys Ser
            45                  50                  55 acc ggc cgg ctg agc acc tcg tgg acc gag gag gac gtg aat gac aac       246
```

|  |  |
|---|---|
| Thr Gly Arg Leu Ser Thr Ser Trp Thr Glu Glu Asp Val Asn Asp Asn<br>        60                        65                      70 |  |
| aca ctc ttc aag tgg atg att ttc aac ggg ggc gcc ccc aac tgc atc<br>Thr Leu Phe Lys Trp Met Ile Phe Asn Gly Gly Ala Pro Asn Cys Ile<br> 75                       80                      85 | 294 |
| ccc tgt aaa gaa acg tgt gag aac gtg gac tgt gga cct ggg aaa aaa<br>Pro Cys Lys Glu Thr Cys Glu Asn Val Asp Cys Gly Pro Gly Lys Lys<br> 90                       95                    100                  105 | 342 |
| tgc cga atg aac aag aag aac aaa ccc cgc tgc gtc tgc gcc ccg gat<br>Cys Arg Met Asn Lys Lys Asn Lys Pro Arg Cys Val Cys Ala Pro Asp<br>                110                    115                    120 | 390 |
| tgt tcc aac atc acc tgg aag ggt cca gtc tgc ggg ctg gat ggg aaa<br>Cys Ser Asn Ile Thr Trp Lys Gly Pro Val Cys Gly Leu Asp Gly Lys<br>                125                    130                    135 | 438 |
| acc tac cgc aat gaa tgt gca ctc cta aag gca aga tgt aaa gag cag<br>Thr Tyr Arg Asn Glu Cys Ala Leu Leu Lys Ala Arg Cys Lys Glu Gln<br>                140                    145                    150 | 486 |
| cca gaa ctg gaa gtc cag tac caa ggc aga tgt aaa aag act tgt cgg<br>Pro Glu Leu Glu Val Gln Tyr Gln Gly Arg Cys Lys Lys Thr Cys Arg<br>                155                    160                    165 | 534 |
| gat gtt ttc tgt cca ggc agc tcc aca tgt gtg gtg gac cag acc aat<br>Asp Val Phe Cys Pro Gly Ser Ser Thr Cys Val Val Asp Gln Thr Asn<br>170                      175                    180                    185 | 582 |
| aat gcc tac tgt gtg acc tgt aat cgg att tgc cca gag cct gct tcc<br>Asn Ala Tyr Cys Val Thr Cys Asn Arg Ile Cys Pro Glu Pro Ala Ser<br>                    190                    195                    200 | 630 |
| tct gag caa tat ctc tgt ggg aat gat gga gtc acc tac tcc agt gcc<br>Ser Glu Gln Tyr Leu Cys Gly Asn Asp Gly Val Thr Tyr Ser Ser Ala<br>                205                    210                    215 | 678 |
| tgc cac ctg aga aag gct acc tgc ctg ctg ggc aga tct att gga tta<br>Cys His Leu Arg Lys Ala Thr Cys Leu Leu Gly Arg Ser Ile Gly Leu<br>                220                    225                    230 | 726 |
| gcc tat gag gga aag tgt atc aaa gca aag tcc tgt gaa gat atc cag<br>Ala Tyr Glu Gly Lys Cys Ile Lys Ala Lys Ser Cys Glu Asp Ile Gln<br>                235                    240                    245 | 774 |
| tgc act ggt ggg aaa aaa tgt tta tgg gat ttc aag gtt ggg aga ggc<br>Cys Thr Gly Gly Lys Lys Cys Leu Trp Asp Phe Lys Val Gly Arg Gly<br>250                      255                    260                    265 | 822 |
| cgg tgt tcc ctc tgt gat gag ctg tgc cct gac agt aag tcg gat gag<br>Arg Cys Ser Leu Cys Asp Glu Leu Cys Pro Asp Ser Lys Ser Asp Glu<br>                    270                    275                    280 | 870 |
| cct gtc tgt gcc agt gac aat gcc act tat gcc agc gag tgt gcc atg<br>Pro Val Cys Ala Ser Asp Asn Ala Thr Tyr Ala Ser Glu Cys Ala Met<br>                285                    290                    295 | 918 |
| aag gaa gct gcc tgc tcc tca ggt gtg cta ctg gaa gta aag cac tcc<br>Lys Glu Ala Ala Cys Ser Ser Gly Val Leu Leu Glu Val Lys His Ser<br>                300                    305                    310 | 966 |
| gga tct tgc aac tga atctgcccgt aaaacctgag ccattgattc ttcagaactt<br>Gly Ser Cys Asn<br>                315 | 1021 |
| tctgcagttt ttgacttcat agattatgct ttaaaaaatt tttttttaact tattgcataa | 1081 |
| cagcagatgc caaaaacaaa aaaagcatct cactgcaagt cacataaaaa tgcaacgctg | 1141 |
| taatatggct gtatcagagg gctttgaaaa catacactga gctgcttctg cgctgttgtt | 1201 |
| gtccgtattt aaacaacagc tcccctgtat tcccccatct agccatttcg gaagacaccg | 1261 |
| aggaagagga ggaagatgaa gaccaggact acagctttcc tatatcttct attctagagt | 1321 |
| ggtaaactct ctataagtgt tcagtgttca catagccttt gtgcaaaaaa aaaaaaaaaa | 1381 |

```
aaaaa                                                            1386
```

<210> SEQ ID NO 6
<211> LENGTH: 317
<212> TYPE: PRT
<213> ORGANISM: Homo sapiens

<400> SEQUENCE: 6

```
Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
        275                 280                 285

Ala Thr Tyr Ala Ser Glu Cys Ala Met Lys Glu Ala Ala Cys Ser Ser
290                 295                 300

Gly Val Leu Leu Glu Val Lys His Ser Gly Ser Cys Asn
305                 310                 315
```

<210> SEQ ID NO 7
<211> LENGTH: 22
<212> TYPE: DNA
<213> ORGANISM: Mus musculus

<400> SEQUENCE: 7

```
aaggctcagc tcatgaacga ct                                         22
```

<210> SEQ ID NO 8
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 8 accccccaggt gtacttctg                                            19

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
catggccgta gggaggtttc                                            20

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 10
gatgacgata tcgctgcgct g                                          21

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11
gtacgaccag aggcatacag g                                          21

<210> SEQ ID NO 12
<211> LENGTH: 62
<212> TYPE: DNA
<213> ORGANISM: Artificial sequence
<220> FEATURE:
<223> OTHER INFORMATION: vector DNA sequence

<400> SEQUENCE: 12
agcttggctc agctcatgaa cgacttcaag agagtcgttc atgagctgag ccttttgga    60 ag                                                                 62

<210> SEQ ID NO 13
<211> LENGTH: 62
<212> TYPE: DNA
<213> ORGANISM: Artificial sequence
<220> FEATURE:
<223> OTHER INFORMATION: vector DNA sequence

<400> SEQUENCE: 13
aattcttcca aaaaggctca gctcatgaac gactctcttg aagtcgttca tgagctgagc    60
ca                                                                  62

TREATMENT OF DUCHENNE MUSCULAR DYSTROPHY WITH MYOBLASTS EXPRESSING DYSTROPHIN AND TREATED TO BLOCK MYOSTATIN SIGNALING

CROSS REFERENCE TO RELATED APPLICATIONS

This application claims the benefit of U.S. Provisional Application No. 60/677,324, filed May 4, 2005, which is incorporated by reference in its entirety. This application is also related to and claims priority to Canadian Application No. 2,538,208, filed Mar. 17, 2006, entitled "Modulation of Myostatin and Use Thereof In Cell Transplantation-Based Treatment of Muscle Disease," with Jacques P. Tremblay and Basma Fatouma Benabdallah listed as inventors, which is also incorporated by reference in its entirety.

FIELD OF THE INVENTION

The invention relates to enhancing muscle mass or prevention or treatment of muscle disease based on a modulation of myostatin signaling, such as for enhancing the proliferation and fusion of transplanted cells.

BACKGROUND OF THE INVENTION

Muscle disease continues to represent a serious health problem. For example, Duchenne muscular dystrophy (DMD) is a severe sex-linked muscle wasting recessive disease affecting 1 in 3500 males at birth (Emery, 1993). It results from a mutation in the gene encoding the muscle protein dystrophin, a 427 kDa protein composed of 3685 amino acids (Hoffman et al., 1987). It is located just beneath the sarcolemma of skeletal myofibers and its absence in DMD patients causes sarcolemmal instability leading to frequent muscle fiber damage and repair (Blau et al., 1983). In dystrophic muscles, regeneration gradually fails and the normal cycle of degeneration-regeneration is tipped in favor of degeneration (Blau et al., 1983). This defective muscle repair due to myoblast senescence leads to death early in the third decade (Ohlendieck and Campbell, 1991). Delivery of normal dystrophin gene by the transplantation of non-dystrophic muscle derived precursor cells (i.e., myoblasts) results in the long-term restoration of this protein. Indeed the transplanted myoblasts fuse with the host fibers and introduce in them the normal dystrophin gene (Skuk and Tremblay, 2000). The success of myoblast transplantation is however reduced by the limited muscle regeneration in mdx mice and in DMD patients (Skuk and Tremblay, 2003). There thus remains a continued need for improved methods for the treatment of muscle disease.

SUMMARY OF THE INVENTION

The invention relates to modulation of myostatin and use thereof, for example for increasing the proliferation and the fusion of transplanted (e.g. muscle precursor cells), for prevention or treatment of muscle disease.

Accordingly, in an aspect, the invention provides a method for increasing the proliferation and/or the fusion of transplanted cells (e.g. muscle precursor cells) thereby to increase muscle mass or to prevent or treat muscle disease associated with a genetic defect, in a subject, the method comprising implanting into the subject a cell comprising a nucleic acid capable of restoring activity corresponding to said genetic defect, the cell having been subjected to a treatment or modification prior to implantation to inhibit myostatin signalling.

In embodiments, the cell is transplanted systemically or intramuscularly in said subject.

In a further aspect, the invention provides a method of increasing growth and/or fusion of a transplanted cell, said cell comprising a nucleic acid (e.g. a normal gene or a transgene) capable of restoring a defective activity due to a genetic defect (i.e. compensating for the genetic defect), in a muscle tissue of a subject suffering from a muscle disease associated with said genetic defect, said method comprising inhibiting myostatin in said cell prior to transplantation, wherein said increase in growth and/or fusion of said cell is favoured over an increase in growth and/or fusion of a corresponding genetically defective cell of said subject.

In a further aspect, the invention provides a cell for implantation into a subject for increasing muscle mass or preventing or treating muscle disease associated with a genetic defect, said cell comprising a nucleic acid capable of restoring activity corresponding to said genetic defect, said cell having been subjected to a treatment or modification prior to implantation to inhibit myostatin signalling.

In an embodiment, the cell is selected from a myocyte, a precursor thereof and a stem cell, e.g. a stem cell capable of fusing with existing muscle fibers or of forming new muscle fibres.

In an embodiment, the above-mentioned disease is a dystrophy. In an embodiment, the dystrophy is Duchenne Muscular dystrophy. In an embodiment the above-mentioned nucleic acid encodes a polypeptide having dystrophin activity. In an embodiment, the above-mentioned disease is selected from hereditary and non-hereditary myopathies.

In an embodiment, the above-mentioned nucleic acid is native to the cell. In an embodiment, the above-mentioned cell comprises a recombinant vector comprising the nucleic acid operably linked to a transcriptional regulatory sequence. In an embodiment, the vector is selected from a plasmid and a viral vector. In an embodiment, the viral vector is selected from: (a) a lentiviral vector; (b) a retroviral vector; (c) an adenoviral vector; (d) an adeno-associated vector; (e) a Herpes vector; (f) a bacculovirus vector; and (g) a hybrid vector composed of any combination of (a) to (f).

In an embodiment, the above-mentioned cell is an autologous cell relative to the subject. In an embodiment, the above-mentioned cell is a heterologous cell relative to the subject. In an embodiment, the above-mentioned cell is allogeneic relative to the subject. In an embodiment, the subject is a mammal, in a further embodiment, a human.

In embodiments, the above-mentioned treatment or modification is selected from: (a) inhibition of myostatin activity; (b) inhibition of activity of a myostatin receptor; (c) inhibition of myostatin expression; (d) inhibition of expression of a myostatin receptor; and (e) any combination of (a) to (d).

In embodiments, the above-mentioned treatment comprises contacting the cell with an agent selected from: (a) an inhibitor of myostatin activity; (b) an inhibitor of activity of a myostatin receptor; (c) an inhibitor of myostatin expression; (d) an inhibitor of expression of a myostatin receptor; and (e) any combination of (a) to (d).

In an embodiment, the myostatin receptor is the Activin receptor II B (ActRIIB).

In embodiments, the inhibitor is an inhibitor of myostatin expression. In embodiments, the myostatin inhibitor is selected from an antisense molecule, a siRNA or siRNA-like molecule, a shRNA, a miRNA, follistatin and promyostatin. In embodiments, the myostatin inhibitor is a nucleic acid that is substantially complementary to a portion of an mRNA encoding a myostatin. In embodiments, the myostatin inhibitor is complementary to a portion of a nucleic acid sequence substantially identical to the nucleotide sequence of SEQ ID NO:1. In an embodiment, the portion of an mRNA comprises at least 5 contiguous bases. In embodiments, the siRNA, siRNA-like molecule, shRNA or miRNA molecule is substantially complementary to a portion of an mRNA encoding a myostatin. In embodiments, the siRNA, siRNA-like molecule, shRNA or miRNA molecule is substantially complementary to a portion of an mRNA corresponding to the DNA sequence of SEQ ID NO:1. In embodiments, the siRNA or siRNA-like molecule comprises less than about 30 nucleotides. In embodiments, the siRNA or siRNA-like molecule comprises about 21 to about 23 nucleotides.

In embodiments, the above-mentioned inhibitor is an inhibitor of expression of a myostatin receptor. In embodiments, the inhibitor of expression of a myostatin receptor is selected from a nucleic acid sequence which is selected from an antisense molecule, a siRNA or siRNA-like molecule, shRNA or miRNA. In an embodiment, the antisense molecule is a nucleic acid that is substantially complementary to a portion of an mRNA encoding a myostatin receptor. In an embodiment, the myostatin receptor is the Activin receptor II B (ActRIIB) and the antisense molecule is complementary to a portion of a nucleic acid sequence substantially identical to the nucleotide sequence of SEQ ID NO:3. In an embodiment, the portion of an mRNA comprises at least 5 contiguous bases. In an embodiment, the siRNA, siRNA-like molecule, shRNA or miRNA molecule is substantially complementary to a portion of an mRNA encoding a myostatin receptor. In an embodiment, the myostatin receptor is the Activin receptor II B (ActRIIB) and the siRNA, siRNA-like molecule, shRNA or miRNA molecule is substantially complementary to a portion of an mRNA corresponding to the DNA sequence of SEQ ID NO:3. In an embodiment, the siRNA or siRNA-like molecule comprises less than about 30 nucleotides. In an embodiment, the siRNA or siRNA-like molecule comprises about 21 to about 23 nucleotides.

In embodiments, the above-mentioned modification is selected from: (a) a genetic alteration of a nucleic acid sequence encoding a myostatin or a transcriptional regulatory sequence thereof; (b) a genetic alteration of a nucleic acid sequence encoding a myostatin receptor or a transcriptional regulatory sequence thereof; (c) a genetic modification coding for an antagonist of myostatin such as promyostatin or follistatin; and (d) any combination thereof.

In an embodiment, the genetic alteration is selected from a deletion, substitution, insertion, mutation and disruption.

In an embodiment, the above-mentioned method further comprises treating or modifying the cell prior to implantation to inhibit myostatin signalling.

In a further aspect, the invention provides a method of preparing a cell for transplantation into muscle tissue of a subject, comprising treating or modifying said cell prior to transplantation to inhibit myostatin signalling.

In a further aspect, the invention provides a use of the above-mentioned cell for increasing its proliferation and its fusion in muscle tissue thereby increasing muscle mass or preventing or treating muscle disease associated with a genetic defect.

In a further aspect, the invention provides a package comprising the above-mentioned cell together with instructions for its transplantation for increasing muscle mass or preventing or treating muscle disease associated with a genetic defect.

In a further aspect, the invention provides a composition comprising the above-mentioned cell together with a carrier adapted for transplantation into muscle tissue of a subject.

In a further aspect, the invention provides a culture system comprising a cell for transplantation into a subject for increasing muscle mass or preventing or treating muscle disease associated with a genetic defect, said cell comprising a nucleic acid capable of restoring activity corresponding to said genetic defect; and suitable culture medium comprising an inhibitor of myostatin signalling.

BRIEF DESCRIPTION OF THE DRAWINGS

FIG. 1. Increased skeletal muscle mass in mdx mice carrying a dominant negative form of myostatin receptor (dnActRIIB). (A) Mating diagram to produce dystrophic (mdx) mice carrying a dominant negative form of myostatin receptor (dnActRIIB). (B) Pictures of control mdx/ActRIIB and transgenic mdx/dnActRIIB live mice showing the increased muscling in mice over expressing a dominant negative myostatin receptor. (C) Hematoxylin and eosin coloration of TA muscles cross-sections of control mdx/ActRIIB and transgenic mdx/dnActRIIB mice. Magnification: 20×.

FIG. 2. The presence of a mutated dominant negative myostatin receptor in mdx mice does greatly increase the resistance of TA muscle fibers to damage induced by physical effort. (A) Representative TA muscle cross-sections of control ActRIIB/mdx and transgenic dnActRIIB/mdx mice, stained with Evans blue after the same physical effort (i.e., swimming during 20 min). (B) Graphical representation of the number of damaged fibers in TA muscles of control mdx/ActRIIB and transgenic mdx/dnActRIIB mice. There are two times less damaged fibers in TA muscles of transgenic mdx/dnActRIIB mice than in the TA muscles of mdx/ActRIIB. Magnification: 2.5×.

FIG. 4. Increased graft success in mdx mice transplanted with myoblasts obtained from non-dystrophic mice expressing a dominant negative myostatin receptor (dnActRIIB). (A) Desmin labeling on control (normal ActRIIB) and test (transgenic dnActRIIB) cultures before the transplantation shows that in both cultures 80% of the cells were desmin positives. (B) Immunohistochemical detection of dystrophin on TA muscle sections of mdx mice transplanted with either control ActRIIB (non-mdx) myoblasts or test dnActRIIB (non-mdx) myoblasts. Magnification: 10×. (C) Graphical representation of the number of dystrophin positive fibers in cross-sections of TA muscles transplanted with control and test myoblasts. There is on average 75% more dystrophin positive fibers in TA muscles transplanted with dnActRIIB myoblasts than in TA muscles transplanted with ActRIIB myoblasts. (N=4, test dnActRIIB myoblast transplantation: 168±48 dystrophin positive fibers; control ActRIIB myoblast transplantation: 96±29 dystrophin positive fibers).

FIG. 5. Formation of hypertrophic dystrophin positive fibers in mdx skeletal muscles transplanted with myoblasts obtained from non-dystrophic mice expressing a dominant negative myostatin receptor (dnActRIIB). (A) Immunohistochemical detection of dystrophin on TA muscles sections of mdx mice transplanted with either ActRIIB (non-mdx) myoblasts or dnActRIIB (non-mdx) myoblasts. Magnification: 20×. (B) Graphical representation of the size of dystrophin positive fibers in TA sections transplanted with control (ActRIIB) or test (dnActRIIB) myoblasts. (N=4, test dnActRIIB myoblast transplantation: 166±68 units; control ActRIIB myoblast transplantation: 76±15 units).

FIG. 11. Construction of a lentivirus follistatin vector.

FIG. 12. Immunocytochemistry (A) and Western blot (B) against follistatin on 293T cells transfected with pCMV-eGFP or pCMV-hFst.

FIG. 13. Immunocytochemistry against follistatin on human myoblast cells infected with pCMV-eGFP (A) or pCMV-hFst(B; 24 h, 48 h and 72 h after infection).

FIG. 14. DNA (SEQ ID NO:1) and polypeptide (SEQ ID NO:2) sequences of human myostatin (Genbank accession No. NM_005259).

FIG. 15. DNA (SEQ ID NO:3) and polypeptide (SEQ ID NO:4) sequences of human ActRIIB (Genbank accession No. NM_001106).

FIG. 16. Long term silencing of the mouse ActRIIB gene after synthetic siRNA transfection in murine cells. A) ActRIIB silencing 2 days after siRNA transfection; and B) ActRIIB silencing 5 days after siRNA transfection. The control corresponds to non-transfected cells. Quantitative RT-PCR with mouse ActRIIB set of primers was performed using 1 µg of total RNA extracted from control and siRNA transfected cells. Results were normalized with the β-actin gene amplification level.

FIG. 18. Long term silencing of mouse ActRIIB gene after transfection of plasmid vector expressing a shRNA targeting ActRIIB under the control of the U6 promoter. A) in murine cells. A) ActRIIB silencing 2 days after shRNA transfection; and B) ActRIIB silencing 5 days after shRNA transfection. Quantitative RT-PCR with mouse ActRIIB set of primers was performed using 1 µg of total RNA extracted from control and plasmid nucleofected cells. Results were normalized with β-actin gene amplification level.

FIG. 21. Immunohistochemical detection of dystrophin on TA muscle sections of mdx and mdx over-expressing follistatin mice transplanted with normal myoblasts. (A) Immunohistochemical detection of dystrophin in TA muscles crosssections of control mdx and transgenic mdx/Fst mice. Magnification: 20×. (B) Graphical results reporting the number of dystrophin positive fibers in mdx and mdx/Fst mice.

FIG. 24. GenBank accession # NM_006350. A) Human follistatin DNA (SEQ ID NO:5) and polypeptide (SEQ, ID NO:6) sequences.

DETAILED DESCRIPTION OF THE INVENTION

Figure 3:
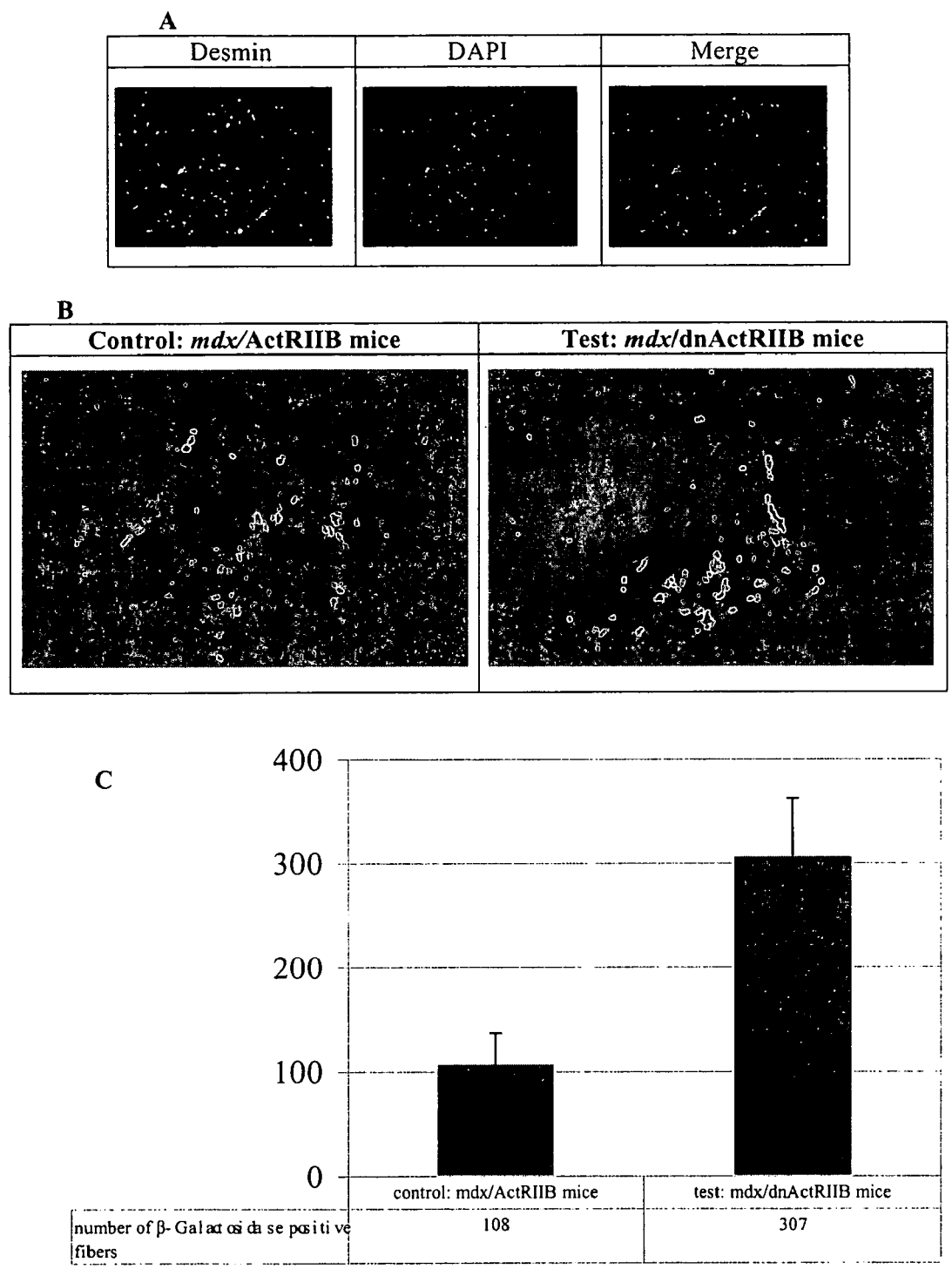
FIG. 3. Improved myoblast graft success in transgenic mdx mice carrying a dominant negative form of myostatin receptor (dnActRIIB). (A) Desmin labeling of normal TnIlacZ myoblast cultures before the transplantation. (B) Histochemistry for β-Gal on TA muscle sections of control mdx (normal ActRIIB) and transgenic mdx (dnActRIIB) mice 21 days after the transplantation of myoblasts obtained from non mdx TnILacZ newborn mice. Magnification: 2.5×. (C) Graphical representation of the number of β-Gal positive fibers in control and test TA muscles sections 21 days after the transplantation of myoblasts from TnILacZ newborn mice. There are on average three fold more β-Gal positive fibers in mdx/dnActRIIB TA muscles than in mdx/normal ActRIIB TA muscles. (N=4, test mdx/dnActRIIB mice: 307±53 β-Gal positive fibers; control mdx/ActRIIB mice: 108±40 β-Gal positive fibers).

Applicants have demonstrated herein that the blockade of myostatin signal in mdx mice or in normal myoblasts results in an increase in the extent of muscle repair and leads to the formation of more dystrophin positive fibers, thus improving the success of myoblast transplantation.

Myostatin, also called Growth and Differentiation Factor-8 (GDF-8), belongs to the TGF-β super family. It is predominantly expressed in developing muscle and in adult skeletal muscle and its activity has been associated with muscle tissue (Jiang et al., 2004; Zhu et al., 2004; Camirand et al., 2004; Hallauer et al., 1993; Lee and Mcherron, 2001; torrente et al., 2001; Hamer et al., 2002; Brussee et al., 1997; Qu-Petersen et al., 2002; Huard et al., 1998); U.S. Pat. No. 6,858,208). Myostatin is initially secreted as a precursor protein composed of two identical 352 amino-acid polypeptide chains, held together by disulphide bonds. The N-terminal 243 amino-acid segments of this dimer, called propeptides, render the myostatin precursor biologically inactive (Jiang et al., 2004). Proteolytic cleavage of these segments generates the mature form of myostatin, which exhibits biological activity only after its complete detachment from the propeptides. Prior to this detachment, the complex is referred to as a 'latency-associated protein' (LAP). After the proteolytic processing, mature myostatin, a 25 kDa protein composed of two identical 109 amino acid polypeptide chains held together by a single disulfide bond, binds to the Activin receptor II B (ActRIIB) to trigger signal transduction. Following binding to its receptor, myostatin activates the signal transduction cascade in the target cells (myoblasts) decreasing their proliferation rate and blocking their terminal differentiation. The signal transduction pathway for myostatin starts with the phosphorylation of the GS domain of the type I receptor by the type II receptor kinase upon ligand binding (Zhu et al., 2004). Both receptor I and II are transmembrane serine/threonine kinase receptors. The activation of the type I receptor initiates specific intracellular signals by cytoplasmic transcription factors, Smads. Indeed, when phosphorylated by the type I receptor kinase, Smad2 and Smad3 bind a Smad4, the activated Smad complex is then translocated into the nucleus and, in conjunction with other nuclear cofactors, regulates the transcription of target genes the signaling cascade of myostatin (Zhu et al., 2004).

Follistatin is a secreted glycoprotein known to antagonise the function of several members of the TGF-β family of secreted signalling factors, including myostatin (Amthor et al., 2004). Indeed, experimental over-expression of follistatin results in muscle enlargement (Lee and McPherron, 2001), whereas follistatin knock-out mice display muscle deficiency (Matzuk et al., 1995). This inhibition occurs after the formation of a latent complex between mature myostatin and follistatin (Gonzalez-Cadavid and Bhasin, 2004).

It was determined via the studies herein that inhibition of myostatin signalling in the context of implantation, e.g. of a cell to be manipulated prior to implantation into a subject, results in improved success in implantation, and thus more effective at eliciting an increase in muscle mass and the regeneration of muscle fiber in the subject. Further, it was determined via the studies herein that the inhibition of myostatin signalling in a cell to be implanted prior to its implantation into a subject is surprisingly more effective at eliciting an increase in muscle mass and the regeneration of muscle fiber in the subject, than global inhibition of myostatin in the subject. Therefore, the inhibition of myostatin signalling in a cell to be transplanted confers a significant advantage in the success of the implantation.

Accordingly, the invention provides methods and materials for increasing or enhancing muscle mass in a subject, and for preventing or treating muscle disease in a subject. The methods provided herein are based on modulation (e.g. inhibition) of myostatin signalling, and cells having a decreased (e.g., lower than wild-type) level of myostatin signalling. Further, the methods described herein may further incorporate gene therapy of a genetic muscle disease.

In embodiments, myostatin signalling may be inhibited by inhibiting myostatin activity and/or expression. For example, myostatin activity on a cell may be inhibited by contacting myostatin with a myostatin inhibitor, e.g. by forming a complex between myostatin and a myostatin inhibitor. Myostatin activity on a cell may also be inhibited by blocking the myostatin receptor ActRIIB Examples of myostatin inhibitors include follistatin, follistatin related protein, G protein-coupled receptor associated sorting protein 1 (GASP-1), and antibodies against myostatin, as well as peptides derived from/fragments of myostatin (e.g. myostatin propeptide), follistatin or follistatin related protein. Another possible approach to inhibit myostatin activity is via the mutation (e.g. disruption, substitution, deletion or insertion) of a nucleic acid encoding a myostatin or a regulatory sequence thereof. Myostatin expression may be inhibited for example by antisense and RNAi methods, as well as via mutation of a nucleic acid encoding a myostatin or a regulatory sequence thereof.

In another embodiment, myostatin may further be inhibited by preventing the cleavage of its inhibitory propeptide. For example, it has been demonstrated that by introducing a mutation at residue ASP$^{76}$, myostatin becomes protease resistant and thus remains in an inactive state.

In further embodiments, myostatin signalling may also be inhibited via the modulation of the expression or activity of another component of the myostatin signalling pathway. For example, myostatin signalling may be inhibited by the inhibition of the activity and/or expression of the myostatin receptor ActRIIB. Another possible approach to inhibit ActRIIB activity is via the mutation (e.g. disruption, substitution, deletion or insertion) of a nucleic acid encoding a ActRIIB or a regulatory sequence thereof. ActRIIB expression may be inhibited for example by antisense and RNAi methods, as well as via mutation of a nucleic acid encoding a ActRIIB or a regulatory sequence thereof.

In a further embodiment, follistatin activity or expression may be modulated in order to modulate myostatin signalling. For example, myostatin signalling may be inhibited via an increase or induction of follistatin activity or expression. Such an increase or induction may be effected for example by contacting a cell with an inducer of follistatin activity, or by increasing follistatin expression in a cell (e.g. by introducing into the cell a vector comprising a nucleic acid encoding a follistatin operably linked to a transcriptional regulatory element [e.g., a promoter] capable of driving the expression of the follistatin-encoding nucleic acid).

In embodiments, the modulation of myostatin signalling comprises the modification or treatment of a cell in order to modulate myostatin signalling in the cell. In embodiments, the cell is a muscle cell or precursor thereof. In a further embodiment, the cell is a myocyte or a precursor thereof. In an embodiment, the cell is a stem cell. In an embodiment, the cell is a mammalian cell, in a further embodiment, a human cell.

The invention provides a method for increasing muscle mass in a subject or for the prevention or treatment of muscle disease in a subject, comprising implanting into the subject the above-noted cell which has been subjected to a treatment or modification to inhibit myostatin signalling. In embodiments, the cell may be implanted into various tissues or body fluids, such as into muscle tissue or blood. In an embodiment, the subject is mammalian, in a further embodiment, human. The cell may be implanted, transplanted or otherwise transferred or introduced into the subject using conventional methods, such as via direct injection to the site of action or surgical methods.

In embodiments, the cell may be autologous or heterologous to said subject. In further embodiments, the cell may be allogeneic to said subject.

In an embodiment, the above-noted muscle disease is a muscular dystrophy associated with a genetic defect such as Duchenne Muscular Dystrophy or other muscular dystrophies and the cell comprises a nucleic acid, a normal gene or a transgene capable of restoring activity corresponding to said genetic defect, e.g., by encoding the active version of a protein which is defective or otherwise lacking or absent in said muscle disease. An example of such a protein is dystrophin, which is mutated in Duchenne Muscular Dystrophy. Examples of muscular dystrophies include Duchenne Muscular Dystrophy, Becker Muscular Dystrophy, Limb Girdle Muscular Dystropgy, Facioscapulohumeral Muscular Dystrophy, Oculopharyngeal muscular dystrophy, Emery-Dreifuss muscular dystrophy, Fukuyama-type congenital muscular dystrophy, Miyoshi myopathy, Ullrich congenital muscular dystrophy, Steinert Muscular Dystrophy.

In embodiments, the above-noted nucleic acid capable of restoring activity may be native to said cell, or in further embodiments, may have been introduced into the cell in the form of a vector comprising the nucleic acid operably-linked to a transcriptional regulatory element.

The invention further provides the above-noted cell which has been treated or modified to inhibit myostatin signalling. The invention further provides methods of preparing the above-noted cell comprising subjecting the cell to a treatment or modification to inhibit myostatin signalling. The invention further provides a culture system for the preparation of said cell comprising an inhibitor of myostatin signalling. The invention further provides uses of the above-noted cell for example in implantation, transplantation and other types of transfer methods for increasing muscle mass in a subject or for the prevention or treatment muscle disease, comprising implantation or transplantation of the cell into a subject in need thereof.

The invention further provides a composition comprising the above-noted cell and a suitable carrier, such as a pharmaceutically acceptable or biocompatible carrier. In an embodiment, the carrier is adapted for the implantation, transplantation or transfer of said cell into a subject.

The invention further provides a package comprising the above-noted cell together with instructions for increasing muscle mass in a subject or for the prevention or treatment muscle disease.

The invention further provides a package comprising the reagents and instructions for the preparation of the above-noted cell. For example, the package may comprise a suitable culture medium and an inhibitor of myostatin signalling, together with instructions for culturing a suitable cell under conditions to obtain a cell in which myostatin signalling is inhibited. The package may further comprise a vector for use in introducing into the cell the above-noted nucleic acid capable of restoring activity corresponding to a genetic defect.

In further embodiments, polypeptides and nucleic acids which are substantially identical to those noted herein may be utilized in the context of the present invention.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term 'homologous' does not infer evolutionary relatedness). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with any of SEQ ID NOs 1-13.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, or at least 95%. Optimal alignment of sequences for comparisons of identity may be conducted using a variety of algorithms, such as the local homology algorithm of Smith and Waterman (1981), the homology alignment algorithm of Needleman and Wunsch (1970), the search for similarity method of Pearson and Lipman (1988), and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (1990) (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff (1992), alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridisation to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (1989). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (1989). Hybridization conditions may be modified in accordance with known methods depending on the sequence of interest (see Tijssen, 1993). Generally, stringent conditions are selected to be about 5° C. lower than the thermal melting point for the specific sequence at a defined ionic strength and pH.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. The term "recombinant" when made in reference to a protein or a polypeptide refers to a protein or polypeptide molecule which is expressed using a recombinant nucleic acid construct created by means of molecular biological techniques. The term "recombinant" when made in reference to genetic composition refers to a gamete or progeny or cell or genome with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

In another aspect of the invention, an isolated nucleic acid, for example a nucleic acid sequence encoding a peptide compound of the invention, or homolog, fragment or variant thereof, may further be incorporated into a recombinant expression vector. In an embodiment, the vector will comprise transcriptional regulatory sequences or a promoter operably-linked to a nucleic acid comprising a sequence capable of encoding a peptide compound, polypeptide or domain of the invention. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of protein coding sequences with which they are operably-linked.

The recombinant expression vector of the present invention can be constructed by standard techniques known to one of ordinary skill in the art and found, for example, in Sambrook et al. (1989). A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation and selection in bacteria and host cells. In addition, the vectors of the present invention may comprise a sequence of nucleotides for one or more restriction endonuclease sites. Coding sequences such as for selectable markers and reporter genes are well known to persons skilled in the art.

A recombinant expression vector comprising a nucleic acid sequence of the present invention may be introduced into a host cell, which may include a living cell capable of expressing the protein coding region from the defined recombinant expression vector. The living cell may include both a cultured cell and a cell within a living organism. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals. Methods for introducing DNA into mammalian cells in vivo are also known, and may be used to deliver the vector DNA of the invention to a subject for gene therapy for a muscle disease.

As noted above, various methods may be utilized in inhibit the expression of a nucleic acid, including antisense and RNAi approaches.

Therefore, in alternative embodiments, the invention provides antisense molecules and ribozymes for exogenous administration to effect the degradation and/or inhibition of the translation of mRNA of interest. Examples of therapeutic antisense oligonucleotide applications, incorporated herein by reference, include: U.S. Pat. No. 5,135,917, issued Aug. 4, 1992; U.S. Pat. No. 5,098,890, issued Mar. 24, 1992; U.S. Pat. No. 5,087,617, issued Feb. 11, 1992; U.S. Pat. No. 5,166,195 issued Nov. 24, 1992; U.S. Pat. No. 5,004,810, issued Apr. 2, 1991; U.S. Pat. No. 5,194,428, issued Mar. 16, 1993; U.S. Pat. No. 4,806,463, issued Feb. 21, 1989; U.S. Pat. No. 5,286,717 issued Feb. 15, 1994; U.S. Pat. No. 5,276,019 and U.S. Pat. No. 5,264,423; BioWorld Today, Apr. 29, 1994, p. 3.

Preferably, in antisense molecules, there is a sufficient degree of complementarity to the mRNA of interest to avoid non-specific binding of the antisense molecule to non-target sequences under conditions in which specific binding is desired, such as under physiological conditions in the case of in vivo assays or therapeutic treatment or, in the case of in vitro assays, under conditions in which the assays are conducted. The target mRNA for antisense binding may include not only the information to encode a protein, but also associated ribonucleotides, which for example form the 5'-untranslated region, the 3'-untranslated region, the 5' cap region and intron/exon junction ribonucleotides. A method of screening for antisense and ribozyme nucleic acids that may be used to provide such molecules as Shc inhibitors of the invention is disclosed in U.S. Pat. No. 5,932,435.

Antisense molecules (oligonucleotides) of the invention may include those which contain intersugar backbone linkages such as phosphotriesters, methyl phosphonates, short chain alkyl or cycloalkyl intersugar linkages or short chain heteroatomic or heterocyclic intersugar linkages, phosphorothioates and those with $CH_2$—NH—O—$CH_2$, $CH_2$—N($CH_3$)—O—$CH_2$ (known as methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Oligonucleotides having morpholino backbone structures may also be used (U.S. Pat. No. 5,034,506). In alternative embodiments, antisense oligonucleotides may have a peptide nucleic acid (PNA, sometimes referred to as "protein nucleic acid") backbone, in which the phosphodiester backbone of the oligonucleotide may be replaced with a polyamide backbone wherein nucleosidic bases are bound directly or indirectly to aza nitrogen atoms or methylene groups in the polyamide backbone (Nielsen et al., 1991 and U.S. Pat. No. 5,539,082). The phosphodiester bonds may be substituted with structures which are chiral and enantiomerically specific. Persons of ordinary skill in the art will be able to select other linkages for use in practice of the invention.

Oligonucleotides may also include species which include at least one modified nucleotide base. Thus, purines and pyrimidines other than those normally found in nature may be used. Similarly, modifications on the pentofuranosyl portion of the nucleotide subunits may also be effected. Examples of such modifications are 2'-O-alkyl- and 2'-halogen-substituted nucleotides. Some specific examples of modifications at the 2' position of sugar moieties which are useful in the present invention are OH, SH, SCH$_3$, F, OCN, O(CH$_2$)$_n$, NH$_2$ or O(CH$_2$)$_n$ CH$_3$ where n is from 1 to about 10; C$_1$ to C$_{10}$ lower alkyl, substituted lower alkyl, alkaryl or aralkyl; Cl; Br; CN; CF$_3$; OCF$_3$; O-, S-, or N-alkyl; O-, S-, or N-alkenyl; SOCH$_3$; SO$_2$ CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. One or more pentofuranosyl groups may be replaced by another sugar, by a sugar mimic such as cyclobutyl or by another moiety which takes the place of the sugar.

In some embodiments, the antisense oligonucleotides in accordance with this invention may comprise from about 5 to about 100 nucleotide units. As will be appreciated, a nucleotide unit is a base-sugar combination (or a combination of analogous structures) suitably bound to an adjacent nucleotide unit through phosphodiester or other bonds forming a backbone structure.

In a further embodiment, expression of a nucleic acid encoding a polypeptide of interest, or a fragment thereof, may be inhibited or prevented using RNA interference (RNAi) technology, a type of post-transcriptional gene silencing. RNAi may be used to create a pseudo "knockout", i.e. a system in which the expression of the product encoded by a gene or coding region of interest is reduced, resulting in an overall reduction of the activity of the encoded product in a system. As such, RNAi may be performed to target a nucleic acid of interest or fragment or variant thereof, to in turn reduce its expression and the level of activity of the product which it encodes. Such a system may be used for functional studies of the product, as well as to treat disorders related to the activity of such a product. RNAi is described in for example Hammond et al. (2001), Sharp (2001), Caplen et al. (2001), Sedlak (2000) and published US patent applications 20020173478 (Gewirtz; published Nov. 21, 2002) and 20020132788 (Lewis et al.; published Nov. 7, 2002), all of which are herein incorporated by reference. Reagents and kits for performing RNAi are available commercially from for example Ambion Inc. (Austin, Tex., USA) and New England Biolabs Inc. (Beverly, Mass., USA).

The initial agent for RNAi in some systems is thought to be dsRNA molecule corresponding to a target nucleic acid. The dsRNA is then thought to be cleaved into short interfering RNAs (siRNAs) which are 21-23 nucleotides in length (19-21 bp duplexes, each with 2 nucleotide 3' overhangs). The enzyme thought to effect this first cleavage step has been referred to as "Dicer" and is categorized as a member of the RNase III family of dsRNA-specific ribonucleases. Alternatively, RNAi may be effected via directly introducing into the cell, or generating within the cell by introducing into the cell a suitable precursor (e.g. vector encoding precursor(s), etc.) of such an siRNA or siRNA-like molecule. An siRNA may then associate with other intracellular components to form an RNA-induced silencing complex (RISC). The RISC thus formed may subsequently target a transcript of interest via base-pairing interactions between its siRNA component and the target transcript by virtue of homology, resulting in the cleavage of the target transcript approximately 12 nucleotides from the 3' end of the siRNA. Thus the target mRNA is cleaved and the level of protein product it encodes is reduced. RNAi may be effected by the introduction of suitable in vitro synthesized siRNA or siRNA-like molecules into cells.

RNAi may for example be performed using chemically-synthesized RNA (Brown et al., 2002). Alternatively, suitable expression vectors may be used to transcribe such RNA either in vitro or in vivo. In vitro transcription of sense and antisense strands (encoded by sequences present on the same vector or on separate vectors) may be effected using for example T7 RNA polymerase, in which case the vector may comprise a suitable coding sequence operably-linked to a T7 promoter. The in vitro-transcribed RNA may in embodiments be processed (e.g. using E. coli RNase III) in vitro to a size conducive to RNAi. The sense and antisense transcripts are combined to form an RNA duplex which is introduced into a target cell of interest. Other vectors may be used, which express small hairpin RNAs (shRNAs) which can be processed into siRNA-like molecules. Various vector-based methods are described in for example Brummelkamp et al. (2002), Lee et al. (2002), Miyagashi and Taira (2002), Paddison et al. (2002) Paul et al. (2002) Sui et al. (2002) and Yu et al. (2002). Various methods for introducing such vectors into cells, either in vitro or in vivo (e.g. gene therapy) are known in the art.

Accordingly, in an embodiment expression of a nucleic acid encoding a polypeptide of interest, or a fragment thereof, may be inhibited by introducing into or generating within a cell an siRNA or siRNA-like molecule corresponding to a nucleic acid encoding a polypeptide of interest (e.g. myostatin), or a fragment thereof, or to an nucleic acid homologous thereto. "siRNA-like molecule" refers to a nucleic acid molecule similar to an siRNA (e.g. in size and structure) and capable of eliciting siRNA activity, i.e. to effect the RNAi-mediated inhibition of expression. In various embodiments such a method may entail the direct administration of the siRNA or siRNA-like molecule into a cell, or use of the vector-based methods described above. In an embodiment, the siRNA or siRNA-like molecule is less than about 30 nucleotides in length. In a further embodiment, the siRNA or siRNA-like molecule is about 21-23 nucleotides in length. In an embodiment, siRNA or siRNA-like molecule comprises a 19-21 bp duplex portion, each strand having a 2 nucleotide 3' overhang. In embodiments, the siRNA or siRNA-like molecule is substantially identical to a nucleic acid encoding a polypeptide of interest, or a fragment or variant (or a fragment of a variant) thereof. Such a variant is capable of encoding a protein having activity similar to the polypeptide of interest. In embodiments, the sense strand of the siRNA or siRNA-like molecule is substantially identical to SEQ ID NOs: 1 or 3, or a fragment thereof (RNA having U in place of T residues of the DNA sequence).

As used herein "pharmaceutically acceptable carrier" or "excipient" includes any and all solvents, dispersion media, coatings, antibacterial and antifungal agents, physiological media, and the like that are physiologically compatible. In embodiments the carrier is suitable for intravenous or intramuscular administration. Pharmaceutically acceptable carriers include sterile aqueous solutions or dispersions and sterile powders for the extemporaneous preparation of sterile injectable solutions or dispersion. The use of such media and agents, such as for the implantation of cells, is well known in the art. Except insofar as any conventional media or agent is incompatible with a cell of the invention, use thereof in the compositions of the invention is contemplated. Supplementary active compounds can also be incorporated into the compositions.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Example 1

Materials and Methods

Materials: Reagents used in the studies herein were purchased from the following companies: Fetal bovine serum (FBS) from Biomedia (Drummondville, Québec, Canada); penicillin/streptomycin, trypsin, X-Gal from Gibco (Burlington, Ontario, Canada); Hank's balanced salt solution (HBSS), collagenase, Dulbecco's modified Eagle medium (DMEM), Optiprep reagent, gelatin, Evans blue, Notexin from Sigma-Aldrich (St. Louis, Mo.); Dispase from Roche Boehringer (Indianapolis, Ind., USA); hematoxylin from Laboratoire Mat (Beauport, Québec, Canada); eosin from Fisher Scientific (Fair Lawn, N.J., USA); mouse anti-human/mouse desmin antibody from DAKO (A/S, Denmark); rabbit anti-mouse dystrophin was produced in our laboratory as described previously (Camirand et al., 2004). Tacrolimus was obtained from Fujisawa pharmaceutical co. (Osaka, Japan); goat anti-mouse IgG conjugated with Alexa 488, goat anti-rabbit IgG conjugated with Alexa 488 from Molecular probes (Eugene, Oreg., USA).

Animals: All the experiments were approved by the animal care committee of the CHUL (Centre Hospitalier de l'Université Laval). Mdx mice (dystrophic mouse model on a C57BL10J genetic background) were purchased from Jackson Laboratory and reproduced in our animal facility. Transgenic TnI-LacZ mice (Hallauer et al., 1993) on a CD1 background) were provided by K. Hasting (McGill University, Canada). The dnActRIIB transgenic mice (Lee and McPherron, 2001) on C57BL6J genetic background) were provided by Se-Jin Lee (Department of Molecular Biology and Genetics, Johns Hopkins University School of Medicine, Baltimore, Md.).

Generation of dystrophic mice carrying a dominant negative form of myostatin receptor: Non-dystrophic male mice heterozygous for the dominant negative form of myostatin receptor (dnActRIIB) were crossed with mdx female mice. Because the dystrophin gene is carried on the X-chromosome, half of the male progeny had the normal myostatin receptor (mdx/ActRIIB) and the others were heterozygous for the dominant negative myostatin receptor (mdx/dnActRIIB) (FIG. 1A).

Physical effort and Evans blue labeling: Four control mice (mdx/ActRIIB) and four transgenic mice (mdx/dnActRIIB) were submitted to a physical effort consisting of an intense swimming for 20 min (Torrente et al., 2001). Evans blue, a vital stain, was administered intraperitoneally (0.1 mg/10 g of total body weight) to each mouse twenty hours before the effort (Hamer et al., 2002). All mice were sacrificed by $CO_2$ inhalation one hour after the effort. The TA muscles were removed, placed in placed in a 30% sucrose solution overnight, and then frozen in liquid nitrogen and stored at −80'. Ten transverse serial cryostat sections (12 μm) were obtained throughout each muscle and observed under fluorescence microscope. The whole cross-sectional area and the total area labeled by Evans blue (muscle fiber damage staining) were photographed and the number of Evans blue stained fibers corresponding of damaged fibers were counted (Brussee et al., 1997).

Cell Culture:

From newborn mice: Primary muscle cultures were prepared using the preplating technique (Qu-Petersen et al., 2002) from newborn (2-3 days) mice carrying the β-Gal gene under the muscle specific troponin I receptor (TnILacZ) (Huard et al., 1998). The $PP_4$ myogenic cells obtained at the fourth plating were cultured at 37° C. in a humidified atmosphere with 5% $CO_2$ in proliferation medium (DMEM-high glucose) supplemented with 10% FBS and 1% penicillin-streptomycin. Desmin labeling was performed on a sample of the culture before the transplantation to establish the percentage of myoblasts. Cells were frozen in DMEM, 50% FBS and 15% DMSO until the transplantation. Cell viability was assessed using trypan blue staining just before the graft.

From adult transgenic mice: Myoblast cultures were prepared from adult transgenic mice carrying a dominant negative form of the myostatin receptor sacrificed by $CO_2$ inhalation. Hind limb muscles were removed and minced using a scalpel. The muscle tissue was then enzymatically dissociated in HBSS containing 0.20% of collagenase type IV and 0.25% of dispase for 1 h at 37° C. The suspension was then washed twice with HBSS and the viable cells were separated from non-viable cells, non-dissociated muscle and bones using the Optiprep™ reagent according to the manufacturer's instructions. Cells were then suspended in DMEM-high glucose, plated in 0.1% gelatin-coated dishes and cultured in the same conditions as above. After 24 h, non-adherent cells were transferred to other gelatin-coated dishes and the adherent cells were discarded. Desmin labeling and cell viability were also performed before the transplantation.

Desmin labeling: Cells were fixed with ethanol 95% for 15 min, washed three times with PBS. Non specific binding sites were blocked by incubating cells with FBS (10%) in PBS for 30 min. Cells were then incubated with a mouse anti-human/mouse desmin antibody (1/50, 1 hr), followed by a goat anti-mouse IgG conjugated with Alexa 488 (1/300, 1 hr). Nuclei were stained with DAPI (1/10000). Desmin labeling was observed under an ultraviolet lamp microscope using a fluorescein isothiocyanate filter.

Long-Term Transplantation Success:

Transplantation of myoblasts obtained from newborn mice: Animals were deeply anaesthetized with 0.15 ml of ketamine/xylazine (10 mg/ml) prior to all surgeries. Two million myoblasts obtained from TnILacZ newborn mice were transplanted in four 8 weeks old transgenic male mdx mice carrying a dominant negative form of myostatin receptor (dnActRIIB), and as a negative control in four non transgenic 8 weeks old male mdx (thus expressing only the normal myostatin receptor ActRIIB). Just before the transplantation, the cells were detached using a 0.125% trypsin solution, washed and resuspended in HBSS. The cells were slowly injected in the Tibialis anterior (TA) muscles using a glass capillary along the transversal axis in 12 trajectories. Mice were immunosuppressed with daily injection of Tacrolimus (FK506 at 2.5 mg/kg). Twenty-one days after the transplantation, mice were sacrificed by $CO_2$ inhalation. TA muscles were dissected out and placed in a 30% sucrose solution overnight to extract the excess of liquid. Each muscle was then transversely oriented in cryomatrix embedding medium (Shandon) and immediately frozen in liquid nitrogen. Thin frozen sections (12 μm) were cut with a cryomicrotome at −20° C., placed on gelatin-coated slides, and kept frozen at 80°-C. β-gal positive muscle fibers in the cryostat sections resulting from the fusion of donor myoblasts with each other or with the host muscle fibers were revealed by histochemistry using the X-gal substrate. For this reaction, muscle sections were fixed using 0.25% glutaraldehyde for 5 min and stained in 0.4 mM X-Gal in a dark box at room temperature for 24 h. β-gal positive muscle fibers were then counted to evaluate the success of the graft (Kinoshita et al., 1994).

Transplantation of myoblasts obtained from adult transgenic mice: One and a half million myoblasts obtained from non dystrophic adult mice carrying the dominant negative form of myostatin receptor were transplanted in the TA of four 8 weeks old mdx mice. These myoblasts were co-injected with 100 ng of notexin to induce necrosis and regeneration (Huard et al., 1994) following the same protocol as described above. Control mdx mice were injected with myoblasts obtained from non-dystrophic mice carrying only the normal gene of myostatin receptor, ActRIIB. Mice were immunosuppressed with Tacrolimus. Twenty-one days after the transplantation, mice were sacrificed and the TA muscles were frozen in liquid nitrogen. An immunoassay with an anti-mouse dystrophin antibody was performed on muscle cryostat sections.

Immunohistochemical detection of dystrophin. Non specific binding sites were blocked by incubating the cryostat sections with FBS (10%) in PBS for 1 hr. Sections were then incubated with a rabbit anti-mouse dystrophin antibody (1/3000, 1 hr), followed by a goat anti-rabbit IgG conjugated with Alexa 488 (1/300, 1 hr). Dystrophin staining was observed under an ultraviolet lamp microscope using a fluorescein isothiocyanate filter.

Statistical analyses: Using ANOVA test, P values<0.05 were considered statistically significant.

Example 2

Skeletal Muscle Mass Improvement in mdx Mice Carrying a Dominant Negative Form of Myostatin Receptor (dnActRIIB)

F1 mdx male mice expressing a dominant negative form of myostatin receptor (dnActRIIB) had a dramatic increase in muscle mass (FIG. 1B), due to both hyperplasia and hypertrophy. Indeed, the TA sections of these mdx/dnActRIIB mice showed a clear increase of overall cross-sectional area, and of fiber number and size when compared to TA sections of control mdx mice. Moreover, in the TA sections of these mdx/dnActRIIB mice, the inter-fascicle space was absent while it was clearly present in the TA sections of mdx mice with the normal myostatin receptor, ActRIIB (FIG. 1C).

Example 3

Myostatin Inhibition in mdx Mice Greatly Increase the Resistance of TA Muscle Fiber to Damage Induced by a Physical Effort After the same physical effort (i.e., swimming for 20 min), the number of Evans blue stained fibers in (mdx/dnActRIIB) TA muscle cross-sections was greatly decreased compared to the number of Evans blue stained fibers in (mdx/ActRIIB) TA muscle cross-sections. (FIG. 2A). Indeed, in control mice (mdx/ActRIIB) 167±45 fibers were stained with the Evans blue dye, while only 76±7 fibers were stained in test mice (mdx/dnActRIIB) (FIG. 2B). We thus concluded that blocking the myostatin signal in dystrophic mice does increase the TA skeletal mass, and also augment the resistance of muscle fibers to the damage induced by exercise probably by increasing the overall strength of the muscles.

Example 4

Improved Success of Myoblast Transplantation in mdx Mice Carrying a Dominant Negative Form of Myostatin Receptor (dnActRIIB)

To investigate the effect of blocking the myostatin signal in dystrophic mice on the long-term success of the transplantation of normal (i.e., non dystrophic) myoblasts, two million TnILacZ myoblasts (desmin positive cells) (FIG. 3A) carrying the β-gal gene under the control of muscle specific troponin I promoter were transplanted in each TA muscle of transgenic mdx mice carrying the dominant negative form of the myostatin receptor (dnActRIIB) and in the TA muscles of control mdx mice with the normal myostatin receptor (ActRIIB). FIG. 3B illustrates representative cross-sections of transplanted muscles of control mdx/ActRIIB mice and of transgenic mdx/dnActRIIB mice. Analysis of variance indicated that there were on average three fold more β-gal positive muscle fibers in the TA of transgenic mdx/dnActRIIB mice than in the TA of control mdx mice. Indeed, in the control mdx TA, 108±40 β-gal positive fibers were counted, whereas in the transgenic mdx/dnActRIIB TA, 307±53 β-gal positive fibers were detected (FIG. 3C). Thus blocking myostatin in dystrophic host mice permits a significant improvement of the success of normal myoblast transplantation.

Example 5

Enhanced Graft Success in mdx Mice Transplanted with Myoblasts Obtained from Non Dystrophic Mice Expressing a Dominant Negative Myostatin Receptor (dnActRIIB)

mdx mice were used as hosts for the transplantation of myoblasts obtained from non-dystrophic transgenic mice carrying either the dominant negative form of the myostatin receptor (dnActRIIB) or the normal myostatin receptor (ActRIIB). Before the transplantation, an immunoassay anti-desmin was done on a sample of both control and test cells and the percentage of myoblasts (desmin positive cells) was the same in both cultures (FIG. 4A); 80% of the cells in both cultures were desmin positive. Three weeks after the transplantation, an anti-dystrophin immunoassay revealed that more dystrophin positive fibers (168±48) were detected in the muscles cross-sections of mdx mice transplanted with myoblasts obtained from mice expressing the dominant negative myostatin receptor dnActRIIB. Only 96±29 dystrophin positive muscle fibers were detected in the muscles cross-sections of mdx mice transplanted with myoblasts obtained from non-dystrophic mice expressing the normal myostatin receptor (ActRIIB) (FIGS. 4B and C). Thus, there were 75% more dystrophin positive fibers following the transplantation of myoblasts obtained from mice expressing the dominant negative myostatin receptor.

Example 6

Formation of Hypertrophic Dystrophin Positive Fibers in mdx Skeletal Muscles Transplanted with Myoblasts Obtained from Non Dystrophic Mice Expressing a Dominant Negative Myostatin Receptor (dnActRIIB)

In the previous experiment, the sizes of the dystrophin positive fibers were also measured in the TA cross-sections of mdx mice transplanted with myoblasts obtained from control mice (ActRIIB) or from transgenic mice expressing the dominant negative myostatin receptor (dnActRIIB). Interestingly, this analysis showed that the dystrophin positive fibers in the TA muscles transplanted with dnActRIIB transgenic myoblasts were on average 50% larger than those observed in TA muscles transplanted with myoblasts obtained from control non-transgenic mice (FIGS. 5A and B). In addition to the anti-dystrophin immunoassay, hematoxylin-eosin coloration of the adjacent cross-sections of each transplanted muscle confirmed this result (FIG. 5A).

Example 7

Mouse ActRIIB Gene Silencing by Transfection of siRNA in Murine Cells Reduces Myostatin Signalling Using RNA interference technology, expression of the ActRIIB transmembrane receptor was blocked in normal non-dystrophic myoblasts. These experiments showed that siRNA targeting of ActRIIB represses the myostatin negative effect on transplanted myoblasts giving myoblasts a proliferative advantage and allowing the formation of more dystrophin positive fibers.

A synthetic siRNA specific for the mouse ActRIIB gene (GenBank accession # NM_007397) was purchased from Ambion. The sequence corresponding to the target site is: 5'-AAGGCTCAGCTCATGAACGACT-3'(SEQ ID NO:7).

Myoblast primary culture obtained from normal TnIlacZ (Hallauer et al., 1993) newborn (2-3 days) mice were washed in HBSS and plated in six wells plate at 500000 cells per well and maintained in proliferation for 24 h. The cells were then transfected with 0, 75 and 100 pmole of the synthetic siRNA purchased from the Ambion Company using PEI (polyethylenimine). Forty-eight hours post-transfection, the total RNA was extracted from each group of cells using Trizol™ according to the manufacturer's protocol. 1 µg of the total RNA extracted from each condition was reverse transcribed and a PCR was performed on the cDNA to amplify the mRNA of the mouse ActRIIB gene using 5'-ACCCCCAGGTGTACT-TCTG-3' (SEQ ID NO:8) as a forward primer and 5'-CATG-GCCGTAGGGAGGTTTC-3'(SEQ ID NO:9) as a reverse primer. Mouse β-actin mRNA was also amplified as a control using 5'-GATGACGATATCGCTGCGCTG-3'(SEQ ID NO:10) as a forward primer and 5'-GTACGACCAGAG-GCATACAGG-3'(SEQ ID NO:11) as a reverse primer.

Fourty-eight hours after the siRNA transfection, control (0 pmole of siRNA) and siRNA 200 pmole of siRNA) transfected myoblasts were treated for 24 h with 150 ng of recombinant mouse myostatin in serum free DMEM. Cells were then washed with HBSS and sonicated in a protein lysis buffer. 15 ug of total protein were then used for an SDS-PAGE assay against the phosphorylated forms of Smad2/3 using a rabbit anti-mouse pSmad2/3 and an anti-rabbit HRP.

Figure 6:
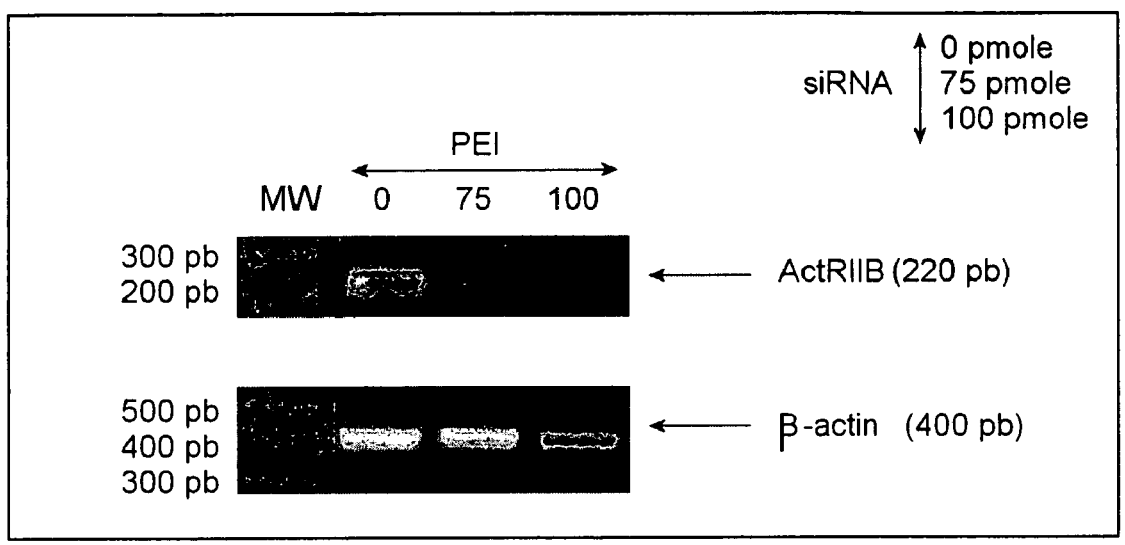
FIG. 6. RT-PCR using 1 µg of total RNA extracted from control and siRNA transfected cells. The top panel was obtained with a set of primers specific for mouse ActRIIB mRNA. The lower panel was obtained from a set of primers specific for mouse β-actin mRNA.

FIG. 6 represents the RT-PCR results and shows that the expression of the ActRIIB gene is significantly decreased in cells transfected with 75 and 100 pmole of siRNA compared with the control cells not transfected with the siRNA. The amplification of the mouse β-actin mRNA is comparable between all conditions.

Figure 7:
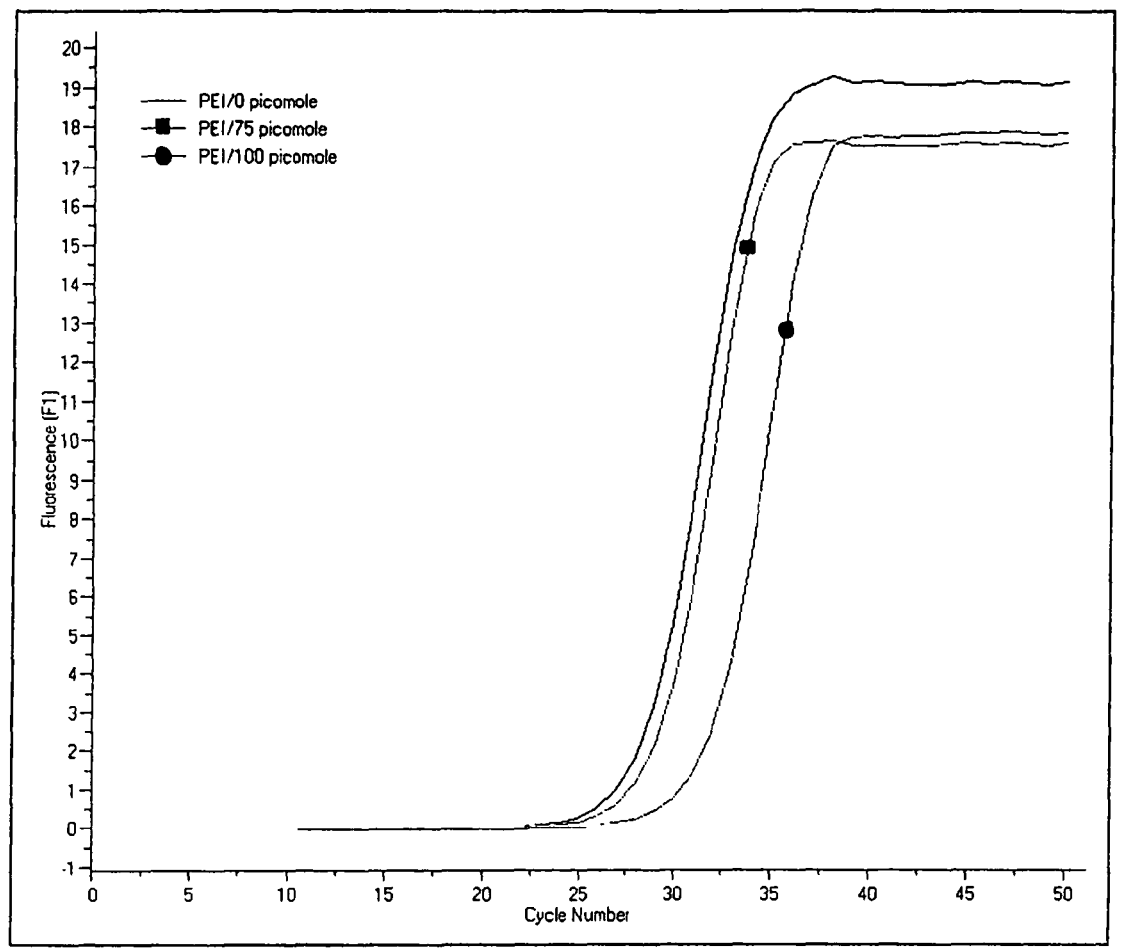
FIG. 7. Quantitative RT-PCR using 1 µg of total RNA extracted from control and siRNA transfected cells with a mouse ActRIIB set of primers and a mouse actin set of primers.

A quantitative PCR was also performed on the same cDNA in order to quantify the ActRIIB mRNA in control and siRNA transfected cells. As represented in FIG. 7, the ActRIIB gene expression was decreased in siRNA transfected cells compared to the control cells.

Long term silencing of the mouse ActRIIB after synthetic siRNA transfection in murine cells was also evaluated by quantitative RT-PCR using 1 µg of total RNA. Results were normalized with the mouse β-actin gene amplification level. FIG. 16 shows that ActRIIB gene silencing persists 5 days after the siRNA transfection. Indeed, 2 days after the siRNA transfection, the number of DNA copies was decreased by about 3 times compared with the control (FIG. 16A); after 5 days, the number of mRNA copies was decreased by about 6 times compared with the non transfected control (FIG. 16B).

Figure 17:
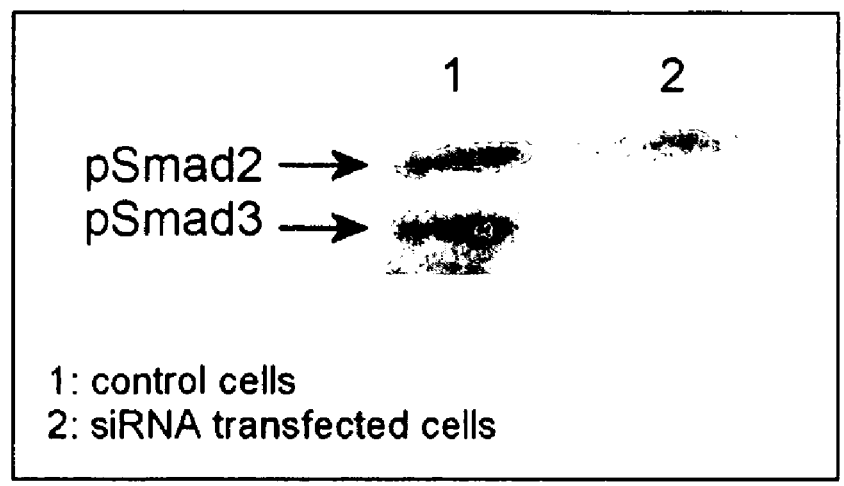
FIG. 17. Western blot against pSmad2/3 of control and siRNA transfected cells treated with recombinant myostatin.

Reduction of myostatin signaling after synthetic siRNA transfection in murine cells was then assessed. Myoblast primary culture obtained from newborn mice were transfected with 200 pmole of the synthetic siRNA using PEI transfection reagent. Control cells were not transfected with the siRNA but received the PEI reagent alone. 48 h post-transfection, cells treated with 150 ng/ml of recombinant myostatin during 24 hours. Protein extracts from control and treated cells were prepared using a lysis buffer, and used for a western blot against the phosphorylated form of Smad2 and Smad3 proteins. FIG. 17 shows that when cells were transfected with the siRNA, there was a decrease in the amount of the pSmad2/3 compared with control cells in which pSmad2/3 were both present.

Example 8

Figure 8:
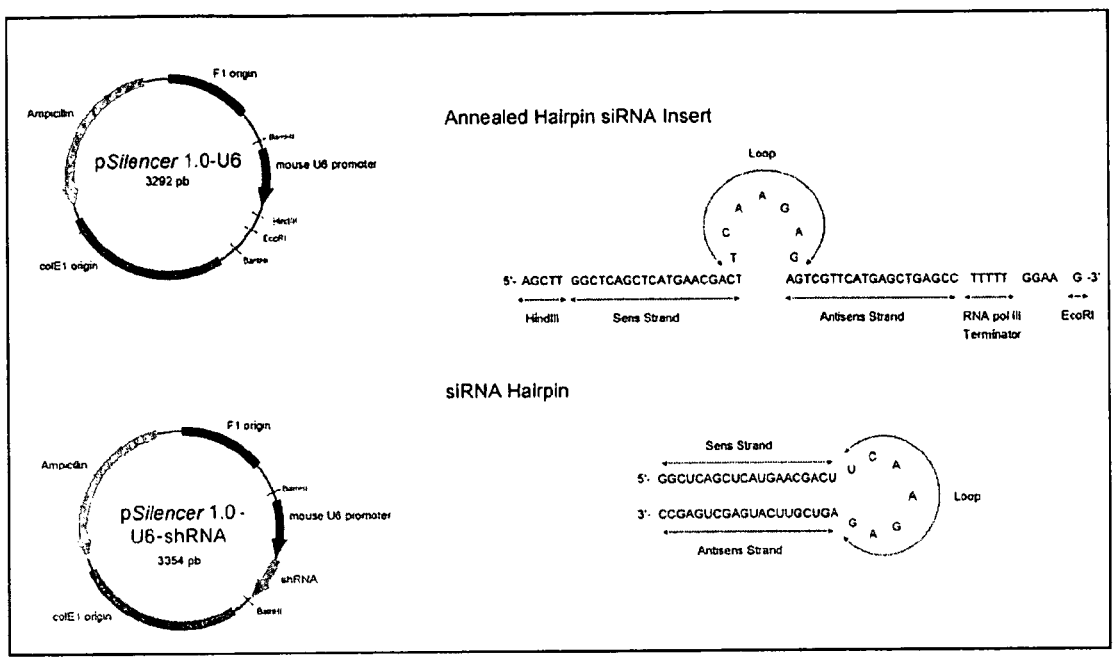
FIG. 8. Construction of a plasmid vector-based siRNA.

RNA Interference with Short Hairpin RNA Transcribed from a Mouse U6 Promoter-Driven Plasmid For the stable synthesis of siRNAs in host cells, transfection of plasmid vectors represents a possible alternative technology to the short-acting siRNA transfection process. siRNAs can be synthesized by plasmid vectors with RNA polymerase III promoter (e.g. U6 promoter) in transfected host cells, and thus effectively suppress target gene expression. For this, a plasmid vector containing the mouse U6 promoter was purchased from Ambion Company (pSilencer 1.0 mouse U6) can be utilized; into which a short hairpin linker is inserted to be controlled by the U6 promoter using HindIII and EcoRI restriction sites. The sense sequence of the polylinker is: 5'-AGCTTGGCTCAGCTCATGAACGACT-TCAAGAGAGTCGTTCATGAGCTGAGC CTTTTTG-GAAG-3' (SEQ ID NO:12), and the antisense sequence is: 5'-AATTCTTCCAAAAAGGCTCAGCTCAT-GAACGACTCTCTTGAAGTCGTTCATGA GCT-GAGCCA-3' (SEQ ID NO:13). See FIG. 8 for a schematic of the construction of a plasmid vector-based siRNA.

Myoblast primary culture obtained from newborn mice were nucleofected with the plasmid vector-based siRNA or with the empty plasmid as a control using the AMAXA™ nucleofector. Total RNA was extracted from control and test cells at different times (2 and 6 days) post-nucleofection.

Quantitative RT-PCR was performed on 1 µg of each RNA extract using mouse ActRIIB and β-actin sets of primers. FIG. 18 shows that the silencing is effectively induced after the nucleofection of the short-hairpin plasmid and also that silencing is persisting 6 days after the plasmid nucleofection. Moreover, 2 days after plasmid nucleofection, the number of mRNA copies was decreased approximately 5 times compared with the control. After 6 days, the number of mRNA copies was still decreased by about 5 times compared with the non transfected control.

Example 9

Lentiviral Delivery of Small Interfering RNA in Mammalian Cells

Figure 9:
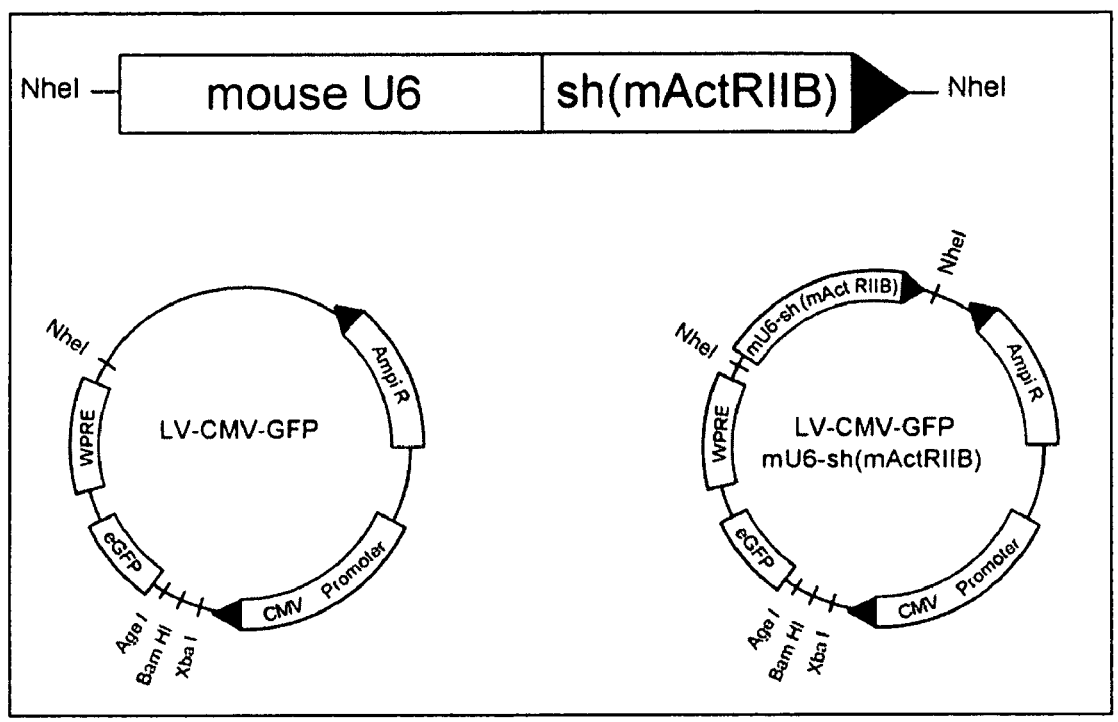
FIG. 9. Construction of a lentivirus vector-based siRNA.

To increase the transfection efficiency or to integrate the shDNA into the genome of host cells, a lentiviral vector-based siRNA may be used. For this, the mouse U6-shRNA insert is amplified by PCR with a primer set containing NheI restriction site at 5'. A LV-CMV-GFP lentivirus is digested with MheI restriction enzyme, and the mouseU6-shRNA insert is ligated in the lentivirus vector to generate a LV-CMV-GFP/mouseU6-shRNA lentivirus vector containing a GFP reporter gene. See FIG. 9 for a schematic of the construction of a lentivirus vector-based siRNA.

Myoblast primary culture obtained from newborn mice are infected with the LV-CMV-GFP U6-shRNA lentivirus and with the LV-CMV-GFP lentivirus as a control. Infected myoblasts are used to perform an in vitro proliferation and a differentiation test and also for in vivo transplantation in mdx mouse muscles to evaluate the success of the transplantation of myoblasts insensitive to the myostatin inhibition. Success of transplantation is evaluated by an immunohistochemistry assay against the dystrophin protein.

Example 10

Figure 19:
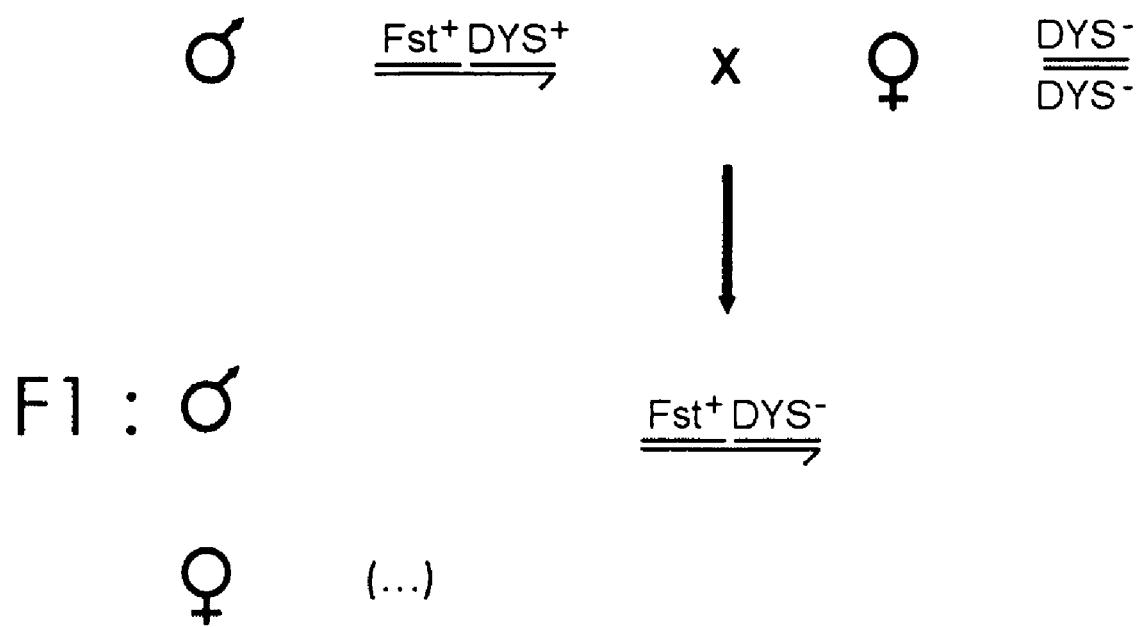
FIG. 19. Mating diagram for the production of dystrophic (mdx) mice over-expressing the follistatin protein.

Improvement of Skeletal Muscle Mass in Dystrophic Mice Over-Expressing Follistatin The effect of follistatin (FIG. 24, GenBank Acc No. NM_6350-a secreted glycoprotein known to antagonise the function of several members of the TGF-β family of secreted signalling factors (Torrente et al., 2001)) on skeletal muscle mass was investigated. Non-dystrophic male mice over-expressing the human follistatin short form protein (Fst) were crossed with mdx female mice. Because the dystrophin gene is carried on the X-chromosome, all of males in the generation F1 were dystrophic. Moreover, all male progenies were transgenic for the follistatin gene (mdx/Fst) because the human follistatin short form gene was also located on the X-chromosome in the non-dystrophic male crossed with the mdx female (FIG. 19).

Figure 10:
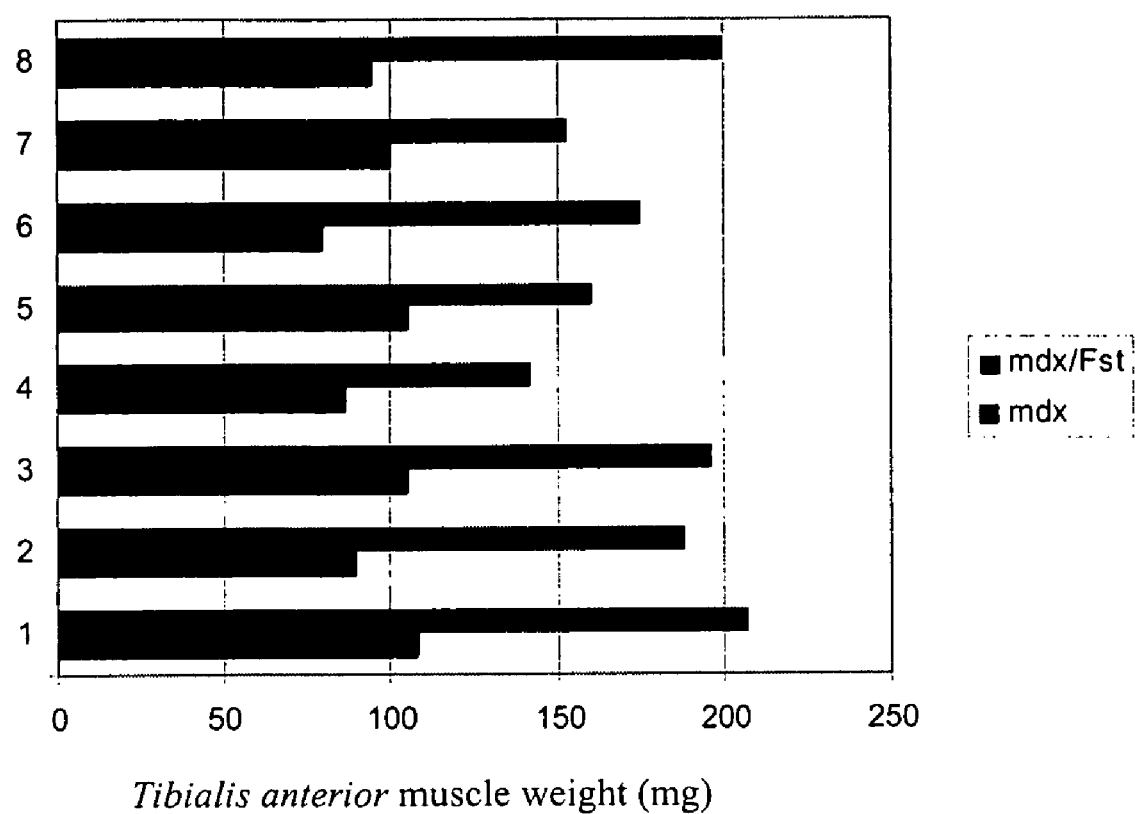
FIG. 10. Graphical results of Tibialis anterior muscle weight in mdx vs. mdx/Fst mice.
Figure 20:
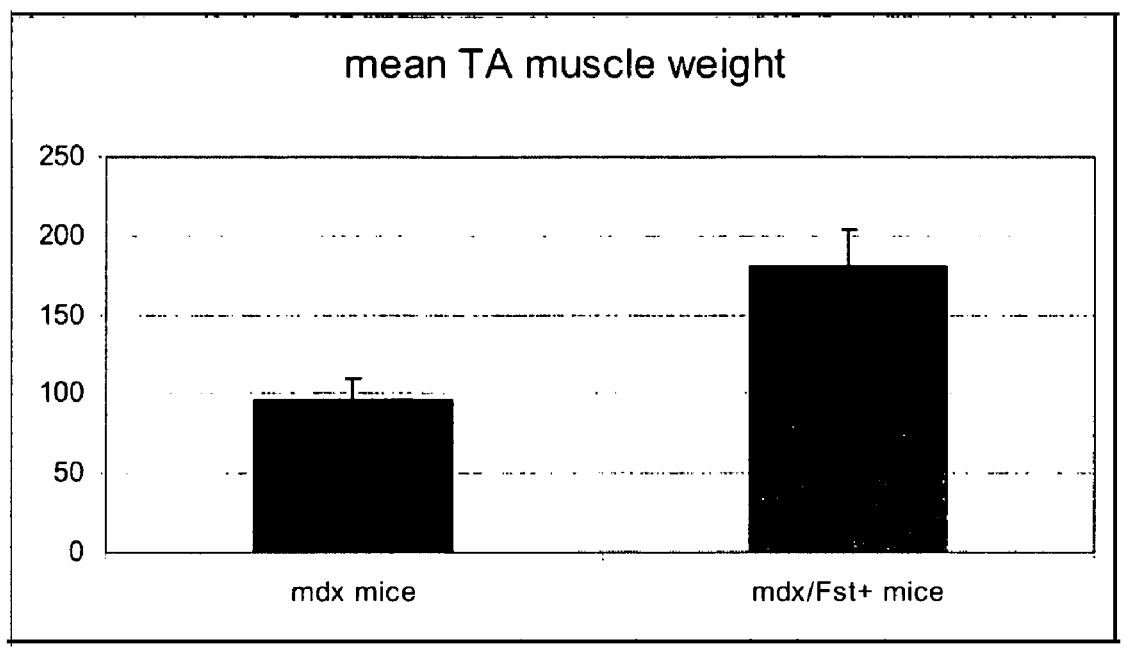
FIG. 20. Graphical results of Tibialis anterior muscle weight in mdx vs. mdx/Fst mice.

The whole body weight and the Tibialis anterior muscle mass of 8 transgenic dystrophic males (mdx/Fst) were initially compared with those of 8 non-transgenic dystrophic males of the same age. Transgenic dystrophic males showed increased muscling, in fact, the Tibialis anterior muscle weight was increased by 186% relative to the control animals (FIGS. 10 and 20).

Example 11

Improvement of Myoblast Transplantation Success in Dystrophic Mice Over-Expressing Follistatin To verify whether the myoblast transplantation success is improved or not in follistatin over-expressing muscle, 2 million normal myoblasts obtained from newborn non dystrophic mice were transplanted in TA muscles of mdx mice and in TA muscles of mdx/Fst mice. The success of the transplantation was evaluated 21 days after the transplantation by determining the number of fibers expressing the dystrophin protein by immuno-histochemistry assay done on transplanted muscle sections. FIGS. 21A and B illustrate representative cross-sections of transplanted muscles of control mdx mice and transgenic mdx/Fst mice. Analysis indicated that there was on average two fold more dystrophin positive muscle fibers in the TA of transgenic mdx mice than in the TA of control mdx mice. Indeed, in the control TA, 145±29 dystrophin positive fibers were counted, whereas in the transgenic Fst TA, 337±38 dystrophin positives fibers were detected (FIG. 21B). Thus blocking myostatin in dystrophic host mice permits a significant improvement of the success of normal myoblast transplantation.

Example 12

Construction of a Lentivirus Coding for the Human Follistatin Short Form Under the Control of a Cytomegalovirus Promoter A lentivirus vector containing a cytomegalovirus promoter controlling the expression of a human follistatin short form gene (SEQ ID NOs:5 and 6) was constructed. First the human follistatin transgene (960 pb) was extracted from a plasmid provided by Dr. Lee (Lee and McPherron, 2001) using Eco RI restriction enzyme (FIG. 11a). The insert was blunted using klenow enzyme. A pCMV-eGFP vector was digested using Sal I and Bam HI enzymes and blunted (FIG. 11b). The follistatin transgene was then cloned in the pCMV vector in order to form the pCMV-hFst lentivirus vector (FIG. 11C). A schematic representation of the construction of the lentivirus follistatin vector is shown in FIG. 11.

Example 13

Over-Expression of the Follistatin Protein in 293T Cells Transfected with the Follistatin Lentivirus 293T cells were transfected with the pCMV-hFst vector using the PEI transfection reagent to produce the follistatin lentivirus. As a control, 293T cells were transfected with the pCMV-eGFP. Follistatin lentivirus and eGFP lentivirus were collected from transfected 293T cells and stored at −80° C. until the infection. An immuno-cytochemistry assay against follistatin protein was performed on pCMV-eGFP and pCMV-hFst transfected 293T cells. The assay showed that pCMV-eGFP transfected cells were follistatin negative, whereas pCMV-hFst transfected cells were all follistatin positive. The protein is thus expressed in transfected cells (FIG. 12A). To confirm the result of the immuno-cytochemistry assay, a western blot was performed on a protein extract sample of each group of cells (eGFP and hFst) (FIG. 12B).

Example 14

Figure 22A:
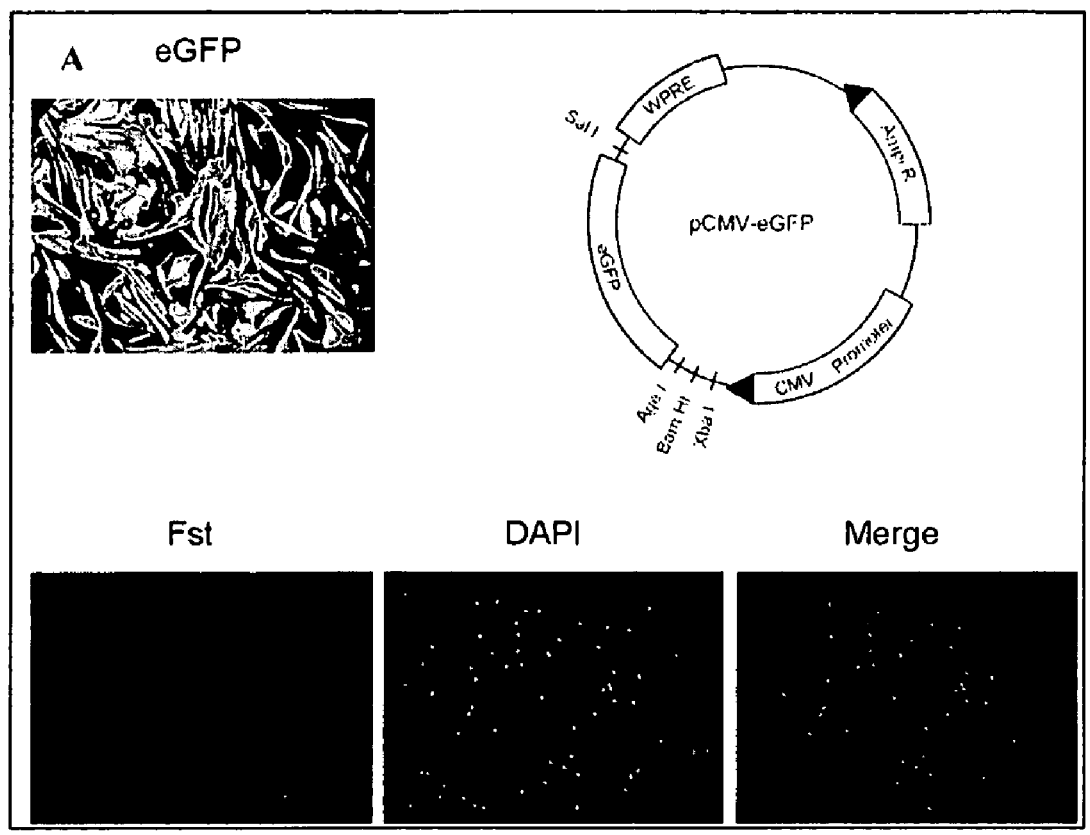
FIG. 22. Immuno-cytochemistry against follistatin on human myoblasts transfected with (A) pCMV-eGFP or (B) pCMV-hFst. (C) Western blot against follistatin protein of myoblasts transfected with pCMV-eGFP or pCMV-hFst.

Over-Expression of the Follistatin Protein in Normal Human Myoblasts Infected with the Follistatin Lentivirus Human myoblasts were infected with lentivirus expressing either eGFP or follistatin. An immuno-cytochemistry assay against follistatin was done on these infected cells 24 h, 48 h and 72 h post infection to evaluate the infection rate, and the follistatin expression level. As shown in FIG. 13, when infected with the follistatin lentivirus, human myoblasts express the follistatin protein at different levels depending of the time course after the infection. 72 h after the infection, the number of marked cells was higher than 24 h or 48 h post-infection (FIG. 13B). In contrast, cells infected with the eGFP lentivirus did not express follistatin (FIG. 13A). The experiment was repeated and expression assessed 48 h post infection. FIG. 22A shows that 48 h post-infection, 100% of cells infected with the eGFP lentivirus were eFGP positive but follistatin negative. FIG. 22B shows that when infected with the follistatin lentivirus, 100% of human myoblasts expressed the follistatin protein 48 h post-infection. Thus, very high rate of infection and expression can be obtained.

To confirm the result of the immuno-cytochemistry assay, a Western blot against follistatin protein was performed on a protein extract sample of each group of cells (pCMV-eGFP and pCMV-hFst transfected 293T cells) (FIG. 22C).

Figure 23:
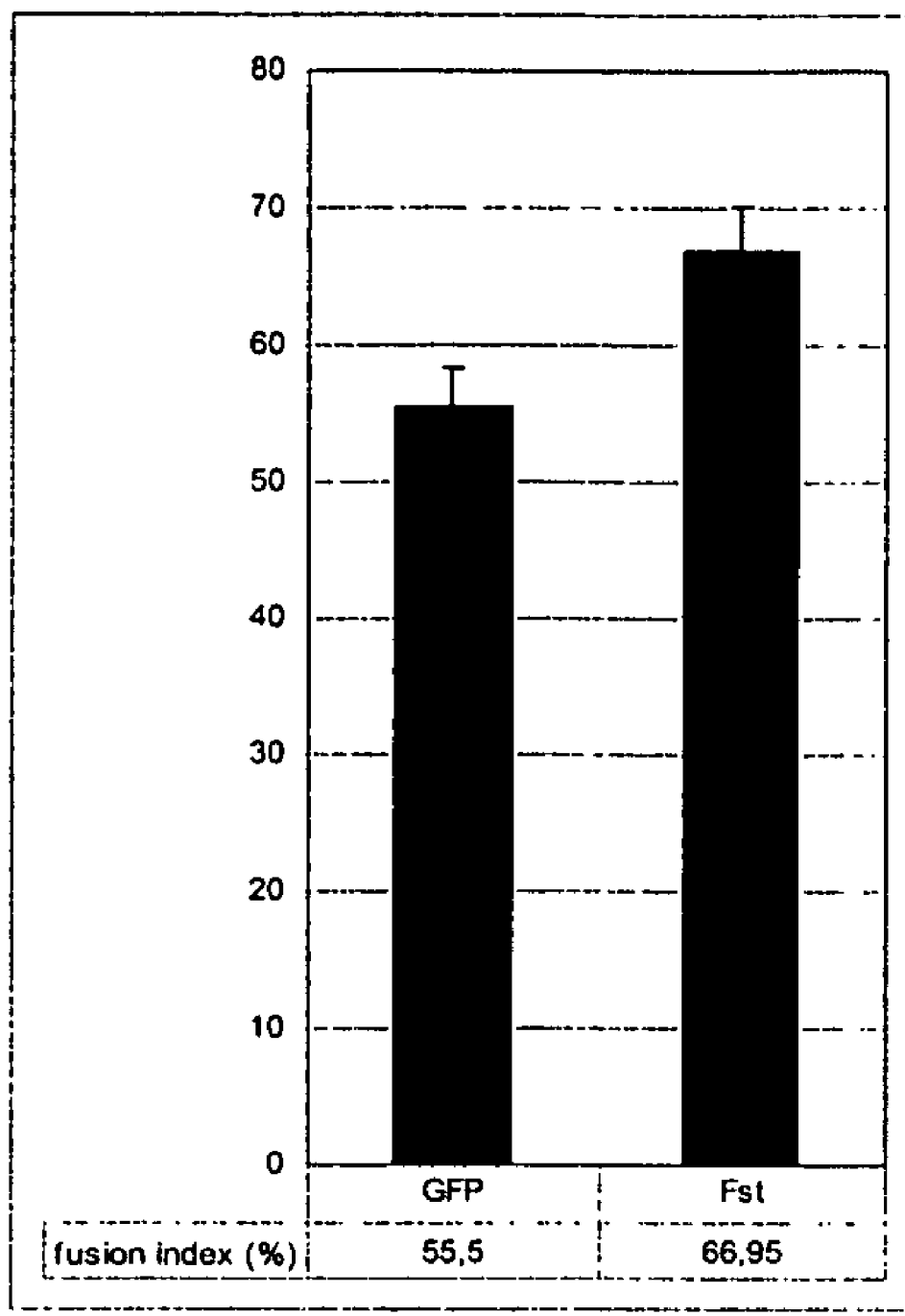
FIG. 23. Fusion index on differentiated human myoblasts injected with pCMV-eGFP or pCMV-hFst.

A fusion assay was also performed on follistatin lentivirus infected and control human myoblasts. Cells were plated in differentiation medium containing 2% of fetal calf serum during 5 days, cells were then fixed and stained with an eosin solution, and nuclei were stained with DAPI. Then the fusion index was calculated in both conditions (pCMV-eGFP and pCMV-hFst infected differentiated myoblasts). Results shown in FIG. 23 clearly indicate that the fusion is improved when the follistatin protein is over-expressed in myoblasts.

Example 15

Transplantation of Human Myoblasts Comprising Lentivirus Expressing Follistatin in TA Muscles of SCID Mice Modified human cells (eGFP or Fst lentivirus infected myoblasts) are transplanted in the TA muscles of SCID (severe combined immune deficiency) mice. Muscle are harvested 21 days after transplantation and success of the graft is evaluated by an immuno-histochemistry assay against human dystrophin protein on muscles cryostat sections.

Applicants have demonstrated herein that the expression of a dominant negative myostatin receptor increased the number and size of the muscle fibers in the mdx mice. This hypertrophy permits to reduce the vulnerability of the dystrophin negative muscle fibers to exercise induced damage. Thus blocking the myostatin signal in Duchenne Muscular Dystrophy patients will reduce the fibrosis and will also prevent the eventual development of the muscle weakness characteristic of this muscular dystrophy.

It is also demonstrated herein that the success of the transplantation of normal myoblasts is improved in mdx mice carrying a dominant negative form of myostatin receptor (mdx/dnActRIIB). The studies herein also demonstrate that normal myoblasts obtained from non-dystrophic transgenic mice carrying the mutated form of myostatin receptor (dnActRIIB) formed more abundant and larger dystrophin positive fibers when transplanted in mdx muscles.

In Example 2 described above, the host mdx mice already had hypertrophied muscle fibers due to the dnActRIIB transgene, β-gal positive fibers were not larger than the β-gal negative muscle fibers in the same muscle. On the other hand, in Examples 3 and 4 described above, when non-dystrophic myoblasts carrying a truncated form of the myostatin receptor were transplanted in dystrophic TA muscles, more abundant and larger dystrophin positive fibers were obtained twenty-one days after the graft. In fact these normal (i.e., non-mdx) myoblasts obtained from transgenic dnActRIIB mice have important proliferative and fusion advantages over the normal myoblasts transplanted in control mice.

Abbreviations Used Herein:
ActRI: Activin receptor type I
ActRIIB: Activin receptor II B
DAPI: 4',6'-diamidino-2-phenylindole hydrochloride
DMD: Duchenne Muscular Dystrophy
DMEM: Dulbecco's modified eagle medium
DMSO: Dimethyl sulfoxide
dnActRIIB: dominant negative activin receptor II B
FBS: Fetal bovine serum
GDF-8: Growth and differentiation factor-8
HBSS: Hank's balanced salt solution
LAP: Latency-associated protein
Mdx: X-linked dystrophic muscular
MyoD: Myo-differentiation
PP: Preplate
Rb: Retinoblastoma protein
TA: Tibialis anterior
TnI-LacZ: Transgenic mouse with the troponin I promoter controlling the LacZ gene Throughout this application, various references are referred to describe more fully the state of the art to which this invention pertains. The disclosures of these references are hereby incorporated by reference into the present disclosure.

REFERENCES

The following references are specifically incorporated herein by reference.
U.S. Pat. No. 4,806,463
U.S. Pat. No. 5,004,810
U.S. Pat. No. 5,034,506
U.S. Pat. No. 5,087,617
U.S. Pat. No. 5,098,890
U.S. Pat. No. 5,135,917
U.S. Pat. No. 5,166,195
U.S. Pat. No. 5,194,428
U.S. Pat. No. 5,264,423
U.S. Pat. No. 5,276,019
U.S. Pat. No. 5,286,717
U.S. Pat. No. 5,539,082
U.S. Pat. No. 5,932,435
U.S. Pat. No. 6,858,208
U.S. Patent Appln. 20020132788
U.S. Patent Appln. 20020173478
Altschul et al., *J. Mol. Biol.*, 215:403-10, 1990.
Amthor et al., *Dev. Biol.*, 270(1) 19, 2004.
Ausubel et al., In: *Current Protocols in Molecular Biology*, John, Wiley & Sons, Inc, New York, 1:2.10.3, 1989.
BioWorld Today, Apr. 29, p. 3, 1994
Blau et al., *Proc. Natl. Acad. Sci. USA*, 80:4856, 1983.
Brown et al., *RNA Interference in Mammalian Cell Culture: Design, Execution and Analysis of the siRNA Effect. Tech-Notes* 9(1): 3-5.
Brummelkamp et al., *Science*, 296(5567):550-553, 2002.
Brussee et al., *Neuromuscul. Disord.*, 7:487, 1997.

Camirand et al., *Am. J. Transplant*, 4:1255, 2004.
Caplen et al., *Proc. Natl. Acad. Sci. USA*, 98:9742-9747, 2001.
Emery, *Neuromuscul. Disord.*, 3:263, 1993.
Gonzalez-Cadavid and Bhasin, *Curr. Opin. Clin. Nutr. Metab. Care*, 7 (4):451, 2004.
Hallauer et al., *Development*, 119:691, 1993.
Hallauer et al., *Development*, 119:691-701, 1993.
Hamer et al., *J. Anat.*, 200:69, 2002.
Hammond et al., *Science*, 293:1146-1150, 2001.
Henikoff and Henikoff, *Proc. Natl. Acad. Sci. USA*, 89:10915-10919, 1992.
Hoffman et al., *Cell*, 51:919, 1987.
Huard et al., *Biochem. Biophys. Res. Commun.*, 248:648, 1998.
Huard et al., *Hum. Gene Ther.*, 5:949, 1994.
Jiang et al., *Biochem. Biophys. Res. Commun.*, 315:525, 2004.
Kinoshita et al., *Muscle Nerve*, 17:975, 1994.
Lee and McPherron, *Proc. Natl. Acad. Sci. USA*, 98(16): 9306, 2001.
Lee et al., *Nat Biotechnol.*, 20(5):500-505, 2002.
Matzuk et al., *Nature*, 374(6520):360, 1995.
Miyagashi and Taira, *Nucleic Acids Res. Suppl.*, (2): 113-114, 2002.
Needleman and Wunsch, *J. Mol. Biol.*, 48:443, 1970.
Nielsen et al., *Science*, 254:1497, 1991.
Ohlendieck and Campbell, *J. Cell Biol.*, 115:1685, 1991.
Paddison et al. *Proc. Natl. Acad. Sci. USA*, 99(3):1443-1448, 2002.
Paul et al., *Nat. Biotechnol.*, 20(5):505-508, 2002.
Pearson and Lipman, *Proc. Natl. Acad. Sci. USA*, 85:2444, 1988.
Qu-Petersen et al., *J. Cell Biol.*, 157:851, 2002.
Sambrook et al., In: *Molecular cloning: a laboratory manual*, $2^{nd}$ Ed., Cold Spring Harbor Laboratory Press, Cold Spring Harbor, N.Y., 1989.
Sedlak (2000).
Sharp P A, *RNA Interference*-2001, *Genes Dev.*, 15: 485-490, 2001.
Skuk and Tremblay, *J. Muscle Res. Cell Motil.*, 24:285, 2003.
Skuk and Tremblay, *Microsc. Res. Tech.*, 48:213, 2000.
Smith and Waterman, *Adv. Appl. Math.*, 2: 482, 1981.
Sui et al. *Proc. Natl. Acad. Sci. USA*, 99(8):5515-5520, 2002.
Tijssen, 1993, In: *Overview of principles of hybridization and the strategy of nucleic acid probe assays*, Elsevier, New York, 1:3, 1993.
Torrente et al., *J. Cell Biol.*, 152:335, 2001.
Yu et al. *Proc. Natl. Acad. Sci. USA*, 99(9):6047-6052, 2002.
Zhu et al., *Cytokine*, 26(6):262, 2004.

What is claimed is:

1. A method of increasing the mass of a muscle tissue or treating Duchenne Muscular Dystrophy (DMD) in a subject suffering from DMD, said method comprising implanting into said muscle tissue of said subject a myoblast, said myoblast being autologous or allogeneic to said subject and comprising a nucleic acid encoding an active dystrophin polypeptide operably linked to a promoter, said myoblast having been subjected to a treatment or modification prior to implantation to inhibit myostatin activity or myostatin ActRIIB receptor activity in said myoblast, whereby said muscle tissue mass is increased or said DMD is treated in said subject.

2. The method of claim 1, wherein said nucleic acid operably linked to a promoter is comprised in a recombinant vector.

3. The method of claim 1, wherein said treatment or modification is selected from the group consisting of:
    (a) inhibition of myostatin activity;
    (b) inhibition of activity of a myostatin ActRIIB receptor;
    (c) inhibition of myostatin expression;
    (d) inhibition of expression of a myostatin ActRIIB receptor; and
    (e) any combination of (a) to (d).

4. The method of claim 3 wherein said treatment comprises contacting said myoblast with an agent selected from the group consisting of:
    (a) an inhibitor of myostatin activity;
    (b) an inhibitor of activity of a myostatin ActRIIB receptor;
    (c) an inhibitor of myostatin expression;
    (d) an inhibitor of expression of a myostatin ActRIIB receptor; and
    (e) any combination of (a) to (d).

5. The method of claim 4, wherein said inhibitor is an inhibitor of myostatin expression.

6. The method of claim 5, wherein said myostatin inhibitor is an oligonucleotide selected from the group consisting of an antisense molecule, a siRNA, siRNA-like molecule, a shRNA, a miRNA and a miRNA-like molecule.

7. The method of claim 6, wherein the oligonucleotide is substantially complementary to a portion of an mRNA encoding a myostatin.

8. The method of claim 6, wherein the antisense molecule is complementary to a portion of a nucleic acid sequence substantially identical to the nucleotide sequence of SEQ ID NO:1.

9. The method of claim 6, wherein the siRNA, siRNA-like molecule, shRNA, miRNA or miRNA-like molecule is substantially identical to a portion of an mRNA encoding a myostatin.

10. The method of claim 6, wherein the siRNA or siRNA-like molecule is substantially complementary to a portion of an mRNA corresponding to the DNA sequence of SEQ ID NO:1.

11. The method of claim 6, wherein the myostatin inhibitor is substantially complementary to a portion of an mRNA encoding a myostatin ActRIIB receptor.

12. The method of claim 4, wherein said inhibitor is an inhibitor of expression of a myostatin ActRIIB receptor.

13. The method of claim 12, wherein said inhibitor of expression of a myostatin ActRIIB receptor is selected from the group consisting of an antisense molecule and an siRNA or siRNA-like molecule.

14. The method of claim 13, wherein the inhibitor of expression is an oligonucleotide that is substantially complementary to a portion of a mRNA encoding a myostatin ActRIIB receptor.

15. The method of claim 13, wherein said antisense molecule is complementary to a portion of a nucleic acid sequence substantially identical to the nucleotide sequence of SEQ ID NO:3.

16. The method of claim 13, wherein the inhibitor of expression is substantially complementary to a portion of an mRNA corresponding to the DNA sequence of SEQ ID NO:3.

17. The method of claim 13, wherein said modification is selected from the group consisting of:
    (a) a genetic alteration of a nucleic acid sequence encoding a myostatin or a transcriptional regulatory sequence thereof;
    (b) a genetic alteration of a nucleic acid sequence encoding a myostatin ActRIIB receptor or a transcriptional regulatory sequence thereof; and
    (c) both (a) and (b).

* * * * *